(12) United States Patent
Williams et al.

(10) Patent No.: US 7,981,159 B2
(45) Date of Patent: Jul. 19, 2011

(54) ANTERO-POSTERIOR PLACEMENT OF AXIS OF ROTATION FOR A ROTATING PLATFORM

(75) Inventors: John L. Williams, Fort Wayne, IN (US); Said T. Gomaa, Fort Wayne, IN (US); Joseph G. Wyss, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 314 days.

(21) Appl. No.: 12/174,507

(22) Filed: Jul. 16, 2008

(65) Prior Publication Data

US 2010/0016978 A1    Jan. 21, 2010

(51) Int. Cl.
*A61F 2/38* (2006.01)
(52) U.S. Cl. ................................... 623/20.21
(58) Field of Classification Search ..... 623/20.15–20.27
See application file for complete search history.

(56) References Cited

U.S. PATENT DOCUMENTS

| | | | |
|---|---|---|---|
| 4,209,861 A | 7/1980 | Walker et al. | |
| 4,215,439 A | 8/1980 | Gold et al. | |
| 4,340,978 A * | 7/1982 | Buechel et al. | 623/20.29 |
| 4,888,021 A | 12/1989 | Forte et al. | |
| 5,071,438 A | 12/1991 | Jones et al. | |
| 5,219,362 A | 6/1993 | Tuke et al. | |
| 5,326,361 A | 7/1994 | Hollister | |
| 5,330,533 A | 7/1994 | Walker | |
| 5,344,460 A | 9/1994 | Turanyi et al. | |
| 5,387,240 A | 2/1995 | Pottenger et al. | |
| 5,395,401 A | 3/1995 | Bahler | |
| 5,413,604 A | 5/1995 | Hodge | |
| 5,549,686 A | 8/1996 | Johnson et al. | |
| 5,571,194 A | 11/1996 | Gabriel | |
| 5,609,643 A | 3/1997 | Colleran et al. | |
| 5,639,279 A | 6/1997 | Burkinshaw et al. | |
| 5,658,342 A * | 8/1997 | Draganich et al. | 623/20.29 |
| 5,683,468 A | 11/1997 | Pappas | |

(Continued)

FOREIGN PATENT DOCUMENTS

DE          19529824 A1       2/1997

(Continued)

OTHER PUBLICATIONS

European Search Report in corresponding European application (i.e., EP 09 16 4478), dated Apr. 28, 2010 (12 pages).

(Continued)

*Primary Examiner* — Suzette J Gherbi
(74) *Attorney, Agent, or Firm* — Maginot, Moore & Beck

(57) ABSTRACT

A knee replacement system includes a femoral component including a lateral condylar articulating portion and a medial condylar articulating portion, a tibial tray including an upper articulating surface, and a tibial insert including (i) a first articulating portion for articulating with the lateral condylar articulating portion with a first condylar dwell point, (ii) a second articulating portion for articulating with the medial condylar articulating portion with a second condylar dwell point, (iii) a lower articulating surface for articulating with the upper articulating surface, and (iv) a coupling member for coupling with the tibial tray and defining an axis of rotation about which the tibial insert rotates with respect to the tibial tray, the axis of rotation intersecting the upper articulating surface at a location posterior to a dwell axis including the condylar dwell points when the dwell axis is projected onto the upper articulating surface.

13 Claims, 12 Drawing Sheets

U.S. PATENT DOCUMENTS

| | | | |
|---|---|---|---|
| 5,702,466 | A | 12/1997 | Pappas et al. |
| 5,755,801 | A | 5/1998 | Walker et al. |
| 5,776,201 | A | 7/1998 | Colleran et al. |
| 5,800,552 | A | 9/1998 | Forte |
| 5,824,102 | A | 10/1998 | Buscayret |
| 5,871,543 | A | 2/1999 | Hofmann |
| 5,871,546 | A | 2/1999 | Colleran et al. |
| 6,013,103 | A | 1/2000 | Kaufman et al. |
| 6,039,764 | A | 3/2000 | Pottenger et al. |
| 6,206,926 | B1 | 3/2001 | Pappas |
| 6,299,646 | B1 | 10/2001 | Chambat et al. |
| 6,379,388 | B1 | 4/2002 | Ensign et al. |
| 6,475,241 | B2 | 11/2002 | Pappas |
| 6,491,726 | B2 | 12/2002 | Pappas |
| 6,589,283 | B1 | 7/2003 | Metzger et al. |
| 6,764,516 | B2 | 7/2004 | Pappas |
| 6,770,099 | B2 | 8/2004 | Andriacchi et al. |
| 6,797,005 | B2 | 9/2004 | Pappas |
| 6,846,329 | B2 | 1/2005 | McMinn |
| 6,916,340 | B2 | 7/2005 | Metzger et al. |
| 6,926,738 | B2 | 8/2005 | Wyss |
| 6,986,791 | B1 | 1/2006 | Metzger |
| 7,025,788 | B2 * | 4/2006 | Metzger et al. ............ 623/20.15 |
| 7,066,963 | B2 | 6/2006 | Naegerl |
| 7,261,740 | B2 | 8/2007 | Tuttle et al. |
| 7,326,252 | B2 * | 2/2008 | Otto et al. .................. 623/20.15 |
| 7,422,605 | B2 | 9/2008 | Burstein et al. |
| 7,572,292 | B2 * | 8/2009 | Crabtree et al. ........... 623/20.24 |
| 2004/0243244 | A1 | 12/2004 | Otto et al. |
| 2005/0096747 | A1 | 5/2005 | Tuttle et al. |
| 2005/0209701 | A1 | 9/2005 | Suguro et al. |
| 2006/0015185 | A1 | 1/2006 | Chambat et al. |
| 2006/0178749 | A1 | 8/2006 | Pendleton et al. |
| 2008/0021566 | A1 | 1/2008 | Peters et al. |
| 2010/0036500 | A1 * | 2/2010 | Heldreth et al. ........... 623/20.31 |

FOREIGN PATENT DOCUMENTS

| | | |
|---|---|---|
| EP | 0732091 A2 | 9/1996 |
| FR | 2417971 A1 | 2/1979 |
| FR | 2787012 A1 | 6/2000 |
| FR | 2835178 | 8/2003 |
| JP | 8500992 T | 2/1996 |
| JP | 2004-167255 | 6/2004 |
| WO | 0209624 | 2/2002 |
| WO | 2007108804 | 9/2007 |

OTHER PUBLICATIONS

European Search Report in corresponding Application (i.e., 09164478.1-2310), mailed on Oct. 20, 2009, 6 pages.

Kurosawa, et al., "Geometry and Motion of the Knee for Implant and Orthotic Design", The Journal of Biomechanics 18 (1985), pp. 487-499, 12 pages.

Barnes, C.L., et al, "Kneeling is Safe for Patients Implanted With Medial-Pivot Total Knee Arthroplasty Designs, Journal of Arthroplasty," vol. 00, No. 0 2010, 1-6, 6 pages.

Blaha, et al., "Kinematics of the Human Knee Using an Open Chain Cadaver Model", Clinical Orthopaedics and Related Research, vol. 410 (2003); 25-34, 10 Pages.

Dennis, et al, "A Multi-Center Analysis of Axial Femorotibial Rotation After Total Knee Arthroplasty", Clinical Orthopaedics 428 (2004): 180-189, 10 Pages.

Fan, Cheng-Yu, et al, "Primitive Results After Medial-Pivot Knee Arthroplasties: A Minimum 5-Year Follow-Up Study," The Journal of Arthroplasty, vol. 25, No. 3 2010, 492-496, 5 Pages.

Freeman, M.A.R., et al, "The Movement of the Normal Tibio-Femoral Joint," The Journal of Biomechanics 38 (2005) (2), pp. 197-208, 3 Pgs.

Fuller, et al., "A Comparison of Lower-Extremity Skeletal Kinematics Measured Using Skin-and Pin-Mounted Markers", Human Movement Science 16 (1997) 219-242, 24 Pages.

Hill, et al., "Tibiofemoral Movement 2: The Loaded and Unloaded Living Knee Studied by MRI", The Journal of Bone & Joint Surgery, vol. 82-B, No. 8 (Nov. 2000), 1196-1198, 3 Pages.

Karachalios, et al., "A Mid-Term Clinical Outcome Study of the Advance Medial Pivot Knee Arthroplasty," WWW.SCIENCEDIRECT.COM, The Knee 16 (2009); 484-488, 5 Pages.

Komistek, et al., "In Vivo Flouroscopic Analysis of the Normal Human Knee", Clinical Orthopaedics 410 (2003): 69-81, 13 Pages.

Komistek, et al., "In Vivo Polyethylene Bearing Mobility is Maintained in Posterior Stabilized Total Knee Arthroplasty", Clinical Orthopaedics 428 (2004): 207-213, 7 Pages.

Koo, et al., "The Knee Joint Center of Rotation is Predominantly on the Lateral Side During Normal Walking", Journal of Biomechanics, vol. 41 (2008): 1269-1273, 5 Pages.

Mannan, et al., "The Medical Rotation Total Knee Replacement: A Clinical and Radiological Review at a Mean Follow-Up of Six Years", The Journal of Bone and Joint Surgery, vol. 91-B, No. 6 (Jun. 2009): 750-756, 7 Pages.

Moonot, et al, "Correlation Between the Oxford Knee and American Knee Society Scores at Mid-Term Follow-Up", The Journal of Knee Surgery, vol. 22, No. 3 (Jul. 2009), 226-230, 5 Pages.

Murphy, Michael Charles, "Geometry and the Kinematics of the Normal Human Knee", Submitted to Masachusetts Institute of Technology (1990), 381 Pages.

Nakagawa, et al., "Tibiofemoral Movement 3: Full Flexion of the Normal Human Knee", J.Bone Joint Surg. Am, vol. 82-B, No. 8 (2000), 1199-1200, 2 Pages.

Omori, et al., "The Effect of Geometry of the Tibial Polyethylene Insert on the Tibiofemoral Contact Kinematics in Advance Medial Pivot Total Knee Arthroplasty", The Journal of Orthopaedics Science (2009) 14:754-760, 7 Pages.

Shakespeare, et al., "Flexion After Total Knee Replacement. A Comparison Between the Medial Pivot Knee and a Posterior Stabilised Knee," WWW.SCIENCEDIRECT.COM, The Knee 13 (2006): 371-372, 3 Pages.

Walker, et al., "Motion of a Mobile Bearing Knee Allowing Translation and Rotation", Journal of Arthroplasty 17 (2002): 11-19, 9 Pages.

Shaw et al., "The Longitudinal Axis of the Knee and the Role of the Cruciate Ligaments in Controlling Transverse Rotation," J.Bone Joint Surg. Am. 1974:56:1603-1609, 7 Pages.

* cited by examiner

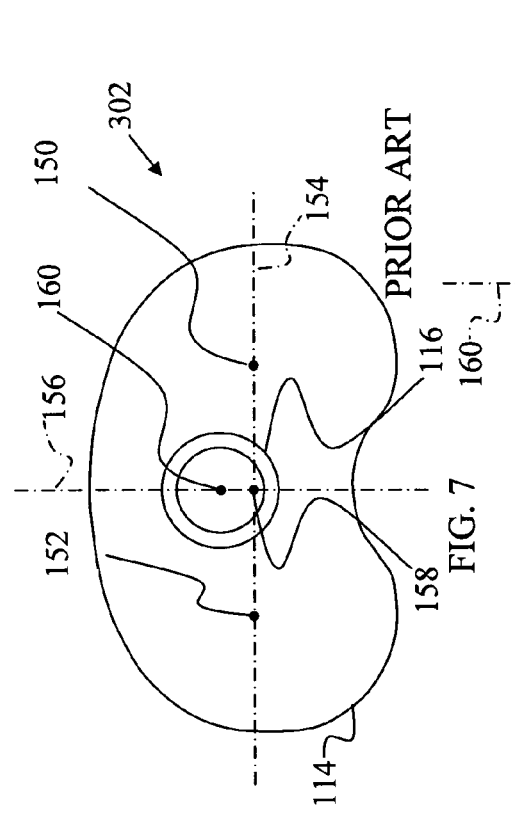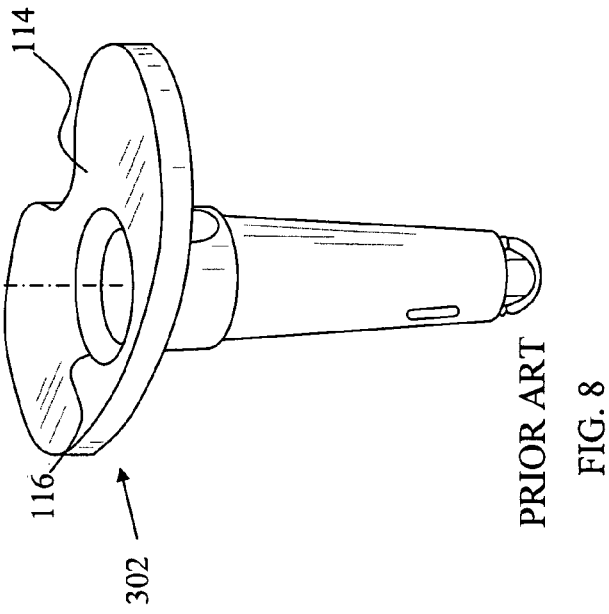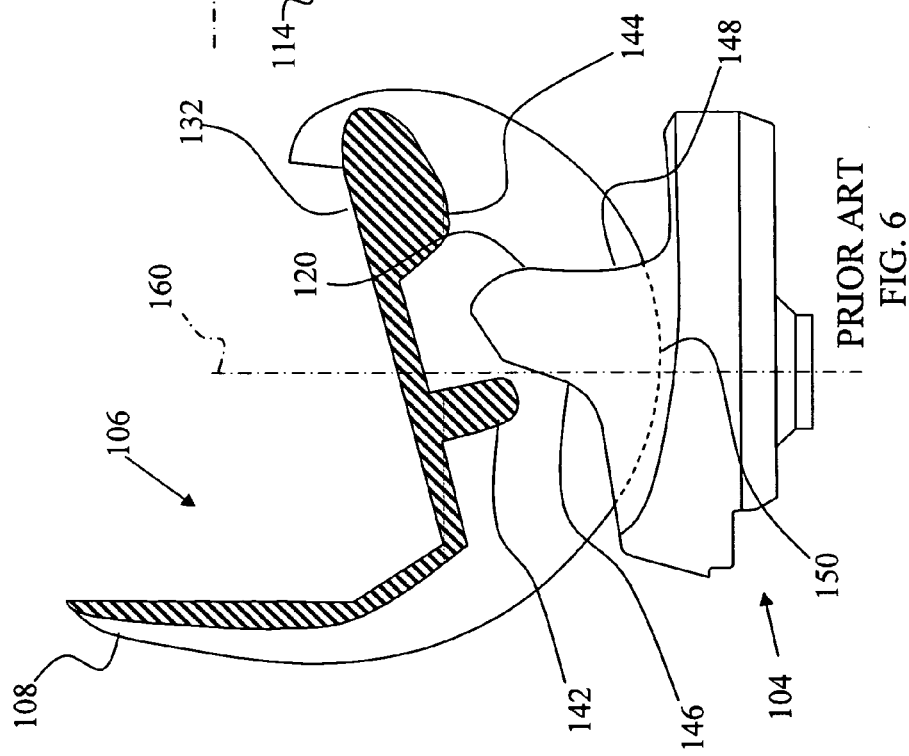

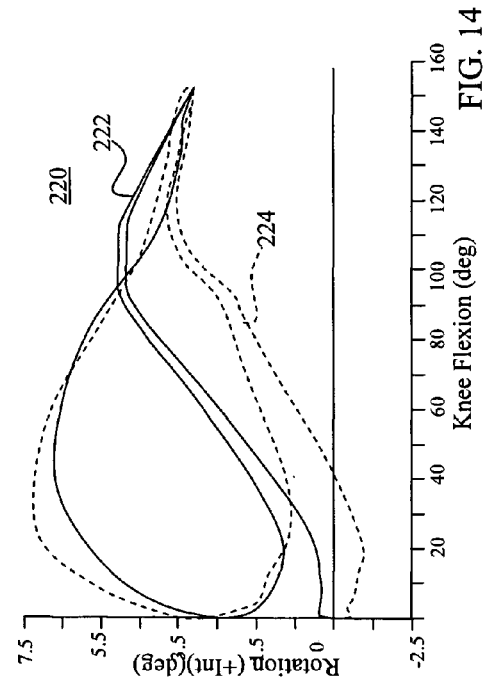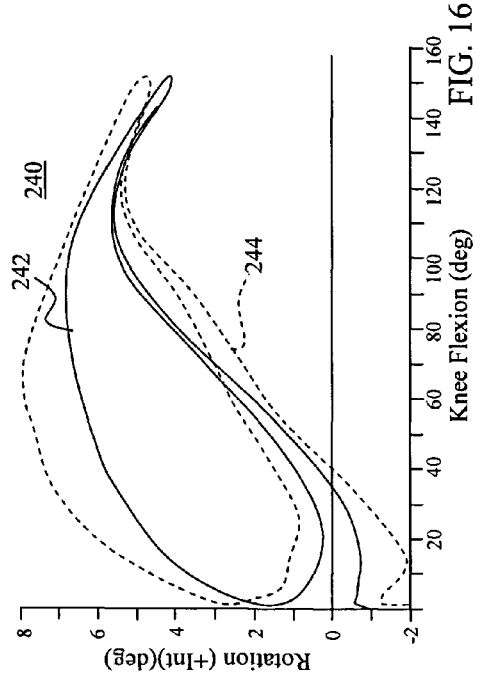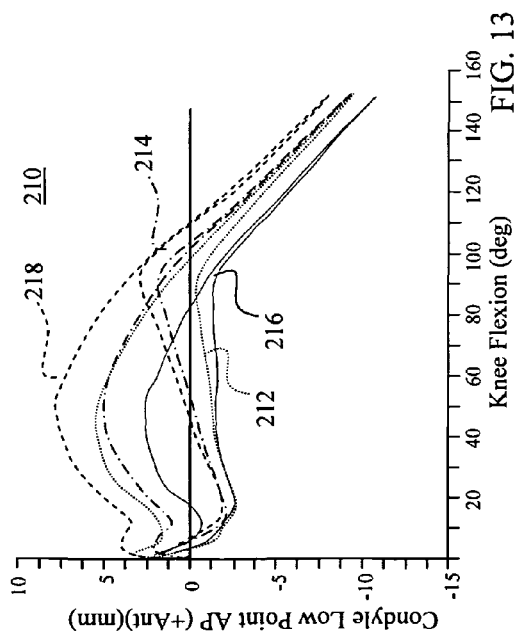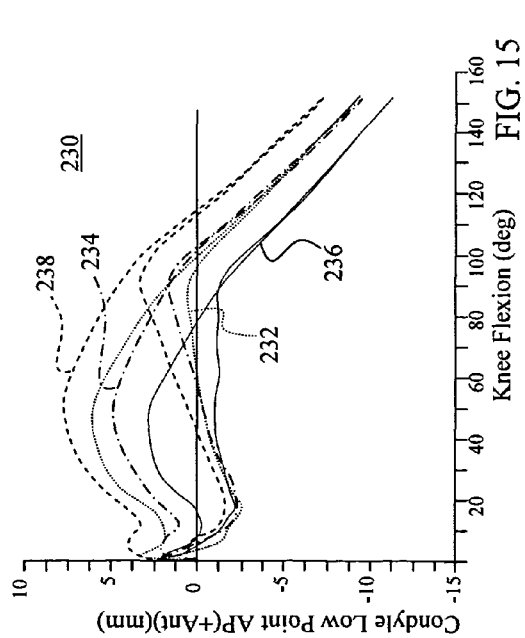
FIG. 13
FIG. 14
FIG. 15
FIG. 16

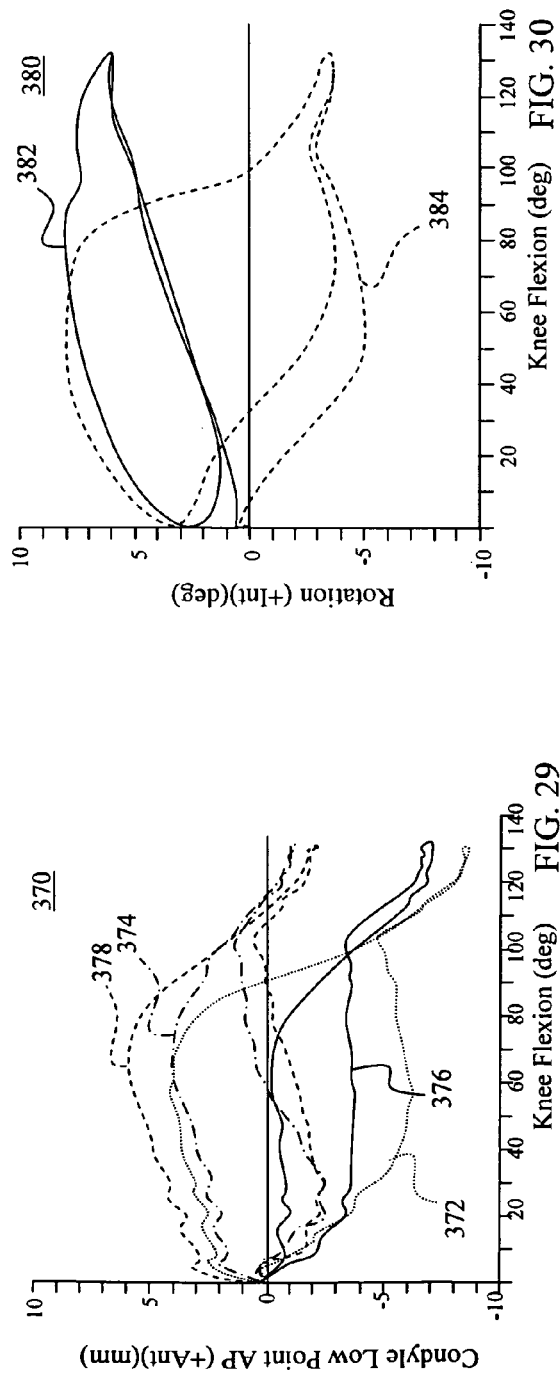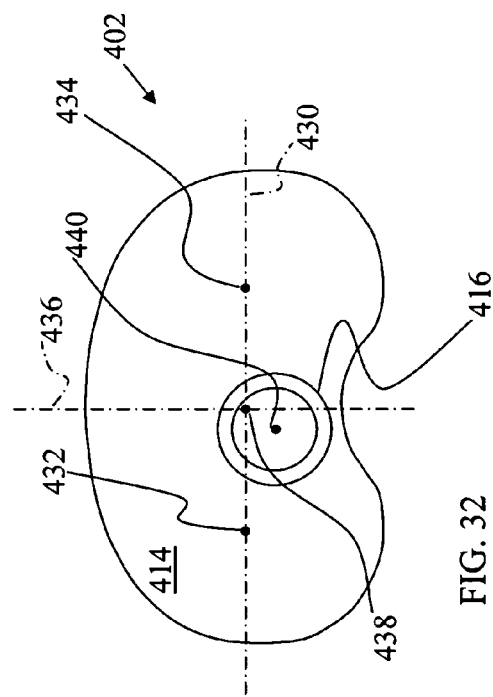

ANTERO-POSTERIOR PLACEMENT OF AXIS OF ROTATION FOR A ROTATING PLATFORM

Cross-reference is made to U.S. Utility patent application Ser. No. 12/165,579entitled "Orthopaedic Femoral Component Having Controlled Condylar Curvature" by John L. Williams et al., which was filed on Jun. 30, 2008, and which was published on Dec. 31, 2009 as U.S. Patent Publication No. 2009/0326667; to U.S. Utility patent application Ser No. 12/165,574 entitled "Posterior Cruciate-Retaining Orthopaedic Knee Prosthesis Having Controlled Condylar Curvature" by Christel M. Wagner, which was filed on Jun. 30, 2008, and which was published on Dec. 31, 2009 as U.S. Patent Publication No. 2009/0326664; to U.S. Utility patent application Ser. No. 12/165,575 entitled "Posterior Stabilized Orthopaedic Knee Prosthesis Having Controlled Condylar Curvature" by Joseph G. Wyss, which was filed on Jun. 30, 2008, and which was published on Dec. 31, 2009 as U.S. Patent Publication No. 2009/0326665; to U.S. Utility patent application Ser No. 12/165,582 entitled "Posterior Stabilized Orthopaedic Prosthesis" by Joseph G. Wyss, which was filed on Jun. 30, 2008 and which was published on Dec. 31, 2009 as U.S. Patent Publication No. 2009/0326666; to U.S. Utility patent application Ser. No. 12/174,539entitled "Knee Prostheses with Enhanced Kinematics" by Joseph G. Wyss, et al., which was filed on Jul. 16, 2008, and which was published on Jan. 21, 2010 as U.S. Patent Publication No. 2010/0016979; and to U.S. Provisional Patent Application Ser. No. 61/077,124 entitled "Orthopaedic Knee Prosthesis Having Controlled Condylar Curvature" by Joseph G. Wyss, which was filed on Jun. 30, 2008; the entirety of each of which is incorporated herein by reference. The principles of the present invention may be combined with features disclosed in those patent applications.

FIELD OF THE INVENTION

This invention relates generally to prostheses for human body joints, and, more particularly, to prostheses for knees.

BACKGROUND OF THE INVENTION

The knee joint provides six degrees of motion during dynamic activities. One such activity is deep flexion or bending of the knee joint. The six degrees of motion are effected by complex movements or kinematics of the bones and soft tissue in the knee joint. Most individuals are capable of controlling the complex movement of a knee joint without thought. The absence of conscious control belies the intricate interactions between a number of different components which are necessary to effect activities such as flexion and extension (when the leg is straightened) of a knee joint.

The knee joint includes the bone interface of the distal end of the femur and the proximal end of the tibia. The patella is positioned over the distal end of the femur and is positioned within the tendon of the long muscle (quadriceps) on the front of the thigh. This tendon inserts into the tibial tuberosity and the posterior surface of the patella is smooth and glides over the femur.

The femur is configured with two large eminences (the medial condyle and the lateral condyle) which are substantially smooth and articulate with the medial plateau and the lateral plateau of the tibia, respectively. The plateaus of the tibia are substantially smooth and slightly cupped thereby providing a slight receptacle for receipt of the femoral condyles. The complex interactions of the femur, the tibia and the patella are constrained by the geometry of the bony structures of the knee joint, the menisci, the muscular attachments via tendons, and the ligaments. The ligaments of the knee joint include the patellar ligament, the medial and lateral collateral ligaments, the anterior cruciate ligament (ACL) and the posterior cruciate ligament (PCL). The kinematics of the knee are further influenced by synovial fluid which lubricates the joint.

A number of studies have been directed to understanding the manner in which the various knee components interact as a knee joint moves through flexion. One such study was reported in an article by P. Johal, et al. entitled "*Tibio-femoral movement in the living knee. A study of weight bearing and non-weight bearing knee kinematics using 'interventional' MRI*, Journal of Biomechanics, Volume 38, Issue 2, Feb. 2005, pages 269-276, which includes a FIG. 2 from which the data set forth in FIG. 1 as graph 10 has been derived. The graph 10 shows the locations of the medial and lateral condyle reference points of a native knee with respect to a tibia as the knee moves through flexion. The line 12 of the graph 10 indicates that the lateral condyle exhibits a constant anterior to posterior translation through deep flexion while the line 14 indicates that the medial condyle remains at about the same location on the tibial plateau until about 90 degrees of flexion. Beyond 90 degrees of flexion, the medial condyle exhibits anterior to posterior translation.

The medial and lateral condyle low (tangency) points are not the actual contact points between the condyles and the femoral plane. Rather, the points represent the lowest portion of the condyle that can be viewed using fluoroscopy. The actual contact point is generally at a location more posterior to the low (tangency) points. Nonetheless, the use of low (tangency) points provides a valid basis for comparison of the effect of changing design variables between components.

Damage or disease can deteriorate the bones, articular cartilage and ligaments of the knee. Such changes from the normal condition of the knee joint can ultimately affect the ability of the natural knee to function properly leading to pain and reduced range of motion. To ameliorate the conditions resulting from deterioration of the knee joint, prosthetic knees have been developed that are mounted to prepared ends of the femur and tibia.

While damage to soft tissue is avoided to the extent possible during knee replacement procedures, some tissue is necessarily sacrificed in replacing a portion of the femur and tibia. Thus, while the typical individual has learned how to coordinate the tensioning of the muscle fibers, ligaments and tendons to provide a smooth transition from a present positioning of the knee to a desired positioning without conscious thought, the sacrifice of tissue changes the physics of the knee. Accordingly, the configuration of soft tissue used to cause movement such as flexion and extension in a healthy knee, or even a pre-operative knee, no longer achieves the same results when the knee is replaced with a prosthesis. Additionally, the sacrifice of soft tissue results in reduced stability of the knee joint.

To compensate for the loss of stability that results from the damage to soft tissue, four general types of implants have been developed. In one approach, the PCL is retained. When the PCL is retained, patients frequently encounter an unnatural (paradoxical) anterior translation of the contact point between the lateral condyle of the femur and the tibia during deep knee-bend movements. Rather than rolling back or slipping as a knee moves through flexion, the femur slides anteriorly along the tibial platform. Paradoxical anterior translation is typically initiated between 30 and 40 degrees of flexion although it can commence at up to about 120 degrees of flexion. The resulting loss of joint stability can accelerate wear, cause a sensation of instability during certain activities of daily living, result in abnormal knee joint motion (kinematics), and/or result in a reduced dynamic moment arm to the quadriceps requiring increased force to control movement.

By way of example, FIG. 2 depicts a sagittal view of a typical prior art femoral component 20 which attempts to mimic the shape of a native knee. The femoral component 20 includes an extension region 22 which is generally anterior to the line 24 and a flexion region 26 which is posterior to the line 24. The extension region 22 is formed with a large radius of curvature ($R_c$) 28 while a small $R_c$ 30 is used in the posterior portion of the flexion region 26 in order to fit within the joint space while providing as much flexion as possible. Contemporaneously with the change of length of the radii of curvature, the origin of the radius of curvature changes from the origin 32 for the $R_c$ 28 to the origin 34 for the $R_c$ 30.

The results of a deep knee bending simulation using a typical prior art femoral component with condylar surfaces in the flexion area defined by a reduced radius of curvature are shown in the translation chart 40 of FIG. 3 which shows the position on the tibial component (y-axis) whereat the medial and lateral condyles contact the tibial component as the device is moved through flexion (x-axis). The simulation was conducted on a multibody dynamics program commercially available from Biomechanics Research Group, Inc. of San Clemente, California, under the name LifeMOD/KneeSIM. The model included tibio-femoral and patello-femoral contact, passive soft tissue, and active muscle elements.

The lines 42 and 44 in the chart 40 show the estimated low (tangency) points for the lateral condylar surface and the medial condylar surface, respectively. Both of the lines 42 and 44 initially track posteriorly (downwardly as viewed in FIG. 3) between 0 degrees and about 30 degrees of flexion. This indicates that the femoral component is rolling posteriorly on the tibial component as the flexion angle increases. Beyond about 30° of flexion, the estimated lateral condyle low (tangency) point line 42 drifts slightly anteriorly from about 5 mm translation while the estimated medial condylar low (tangency) point line 44 moves rapidly anteriorly. Movement of both surfaces in the anterior direction shows that paradoxical anterior translation is occurring beyond about 30 degrees. A comparison of the lines 42 and 44 beyond 30° of flexion with the lines 12 and 14 of FIG. 1 reveals a striking disparity in kinematics between the native knee and the replacement knee which mimics the geometry of the native knee.

Additionally, returning to FIG. 2, as the femoral component 20 is flexed such that contact with a tibial component (not shown) occurs along the condylar surface defined by the $R_c$ 28, the forces exerted by soft-tissues on the knee are coordinated to provide a smooth movement based, in part, upon the length of the $R_c$ 28 and the origin 32. As the femoral component 20 is moved through the angle at which the condylar surface transitions from the $R_c$ 28 to the $R_c$ 30, the knee may initially be controlled as if it will continue to move along the $R_c$ 28. As the femoral component 20 continues to move, the actual configuration of the knee diverges from the configuration that would be achieved if the surface in contact with the tibial component (not shown) was still defined by the $R_c$ 28. When the divergence is sensed, it is believed that the soft-tissue forces are rapidly re-configured to a configuration appropriate for movement along the surface defined by the $R_c$ 30 with the origin 34. This sudden change in configuration, which is not believed to occur with a native knee, contributes to the sense of instability.

Furthermore, Andriacchi, T. P., *The Effect of knee Kinematics, Gait and Wear on the Short and Long-Term Outcomes of primary Total Knee Replacement*, NIH Consensus Development Conference on Total Knee Replacement, pages 61-62, (Dec. 8-10, 2003) reports that in a native knee, flexion between 0 and 120 degrees is accompanied by approximately 10 degrees of external rotation of the femur with respect to the tibia while an additional 20 degrees of external rotation is required for flexion from 120 degrees to 150 degrees. Thus, an initial ratio of about 0.008 degrees of external rotation per degree of flexion is exhibited between 0 degrees and 120 degrees of flexion which increases to a ratio of 0.67 degrees of external rotation per degree of flexion between 120 degrees and 150 degrees of flexion. This rotation allows the knee to move into deep flexion.

The reported external rotation of the native knee is supported by the data in FIG. 1. Specifically, between about 9 degrees and 90 degrees of flexion, the slope of the line 12 is constantly downward indicating that the lowest point of the lateral condylar surface is continuously tracking posteriorly. The line 14, however, is moving anteriorly from about 9 degrees of flexion through 90 degrees of flexion. Thus, assuming this difference to be solely due to external rotation, the femoral component is externally rotating as the knee moved from about 9 degrees of flexion to about 90 degrees of flexion. Beyond 90 degrees of flexion, the lines 12 and 14 show that both condylar surfaces are moving posteriorly. The lateral condylar surface, however, is moving more rapidly in the posterior direction. Accordingly, the gap between the lines 12 and 14 continues to expand beyond 90 degrees, indicating that additional external rotation of the knee is occurring.

FIG. 4 shows the internal rotation of the tibia with respect to the femur (which from a modeling perspective is the same as external rotation of the femur with respect to the tibia, both of which are identified herein as "$\phi_{i-e}$") during the testing that provided the results of FIG. 3. The graph 50 includes a line 52 which shows that as the tested component was manipulated to 130 degrees of flexion, the $\phi_{i-e}$ reached a maximum of about seven degrees. Between about 0 degrees of flexion and 20 degrees of flexion, the $\phi_{i-e}$ varies from 1 degree to zero degrees for a change rate of −0.05 degrees of internal rotation per degree of flexion. Between about 20 degrees of flexion and 50 degrees of flexion, the internal rotation varies from 0 degrees to 1 degree for a change rate of 0.03 degrees of internal rotation per degree of flexion. Between about 50 degrees and 130 degrees, the graph 50 exhibits a nearly linear increase in internal rotation from about 1 degree to about 7 degrees for a change rate of 0.075 degrees of internal rotation per degree of flexion. Accordingly, the $\phi_{i-e}$ of a knee joint incorporating the prior art femoral component differs significantly from the $\phi_{i-e}$ of a native knee.

Various attempts have been made to provide kinematics more akin to those of the native knee. For example, the problem of paradoxical anterior translation in one type of implant is addressed by sacrificing the PCL and relying upon articular geometry to provide stability. In another type of implant, the implant is constrained. That is, an actual linkage is used between the femoral and tibial components. In another type of implant, the PCL is replaced with a cam on the femoral component and a post on the tibial component.

Another attempt to replicate the kinematics of the native knee involves the use of a tibial insert which is configured to rotate upon a tibial plateau. Rotating tibial inserts are commonly referred to as rotating platform (RP) designs. One presumed advantage of RP designs is the decoupling of flexion-extension from $\phi_{i-e}$. This decoupling is believed to reduce total wear of the components. The axis of rotation of the tibial insert on a tibial plateau (RP axis) has typically been positioned between locations coincident with the tibio-femoral dwell points (the low or tangency points of the femoral component when the joint is in full extension) and locations removed from the tibio-femoral dwell points in the anterior direction.

What is needed is a knee prosthesis that more closely reproduces the inherent stability and kinematics of a native knee such as by managing $\phi_{i-e}$. A further need exists for a knee prosthesis that manages $\phi_{i-e}$ while allowing an acceptable rollback of a femoral component on a tibial plateau.

SUMMARY

A knee replacement system with improved kinematics in one embodiment includes a femoral component including a lateral condylar articulating portion and a medial condylar articulating portion, a tibial tray including an upper articulating surface, and a tibial insert including (i) a first articulating portion for articulating with the lateral condylar articulating portion with a first condylar dwell point, (ii) a second articulating portion for articulating with the medial condylar articulating portion with a second condylar dwell point, (iii) a lower articulating surface for articulating with the upper articulating surface, and (iv) a coupling member for coupling with the tibial tray and defining an axis of rotation about which the tibial insert rotates with respect to the tibial tray, the axis of rotation intersecting the upper articulating surface at a location posterior to a dwell axis including the first condylar dwell point and the second condylar dwell point when the dwell axis is projected onto the upper articulating surface.

In a further embodiment, a prosthetic joint includes a femoral component including a lateral condylar articulating portion and a medial condylar articulating portion, a tibial tray including an upper articulating surface, and a tibial insert including (i) a first articulating portion for articulating with the lateral condylar articulating portion, (ii) a second articulating portion for articulating with the medial condylar articulating portion, (iii) a lower articulating surface for articulating with the upper articulating surface, and (iv) a pivot defining an axis of rotation about which the tibial insert rotates with respect to the tibial tray, the axis of rotation intersecting the upper articulating surface at a location lateral to a tibial insert centerline when the centerline is projected onto the upper articulating surface.

In a further embodiment, a prosthetic joint includes a femoral component including a lateral condylar articulating portion and a medial condylar articulating portion, a tibial tray including an upper articulating surface, and a tibial insert including (i) a first articulating portion for articulating with the lateral condylar articulating portion with a first condylar dwell point, (ii) a second articulating portion for articulating with the medial condylar articulating portion with a second condylar dwell point, (iii) a lower articulating surface for articulating with the upper articulating surface, and (iv) a coupling member for coupling with the tibial tray and defining an axis of rotation about which the tibial insert rotates with respect to the tibial tray, the axis of rotation intersecting the upper articulating surface at a location posterior to a dwell axis including the first condylar dwell point and the second condylar dwell point when the dwell axis is projected onto the upper articulating surface and lateral to a tibial insert centerline when the centerline is projected onto the upper articulating surface.

The above-described features and advantages, as well as others, will become more readily apparent to those of ordinary skill in the art by reference to the following detailed description and accompanying drawings.

BRIEF DESCRIPTION OF THE DRAWINGS

FIG. 6 depicts a sagittal view of the prior art knee prosthesis of FIG. 5 showing a condylar dwell point located posterior to the axis of rotation;

FIG. 7 depicts a top plan view of the dwell axis and the centerline of the tibial insert of the prior art knee prosthesis of FIG. 5 projected onto the articulating surface of the tibial tray of the prior art knee prosthesis of FIG. 5;

FIG. 8 depicts a perspective view of the tibial tray of the prior art knee prosthesis of FIG. 5 with the coupler member defining an axis of rotation for the tibial bearing insert;

FIG. 13 shows a graph of the results of a deep knee bending simulation using the prior art knee replacement system of FIG. 9 and modified to have an axis of rotation of the tibial bearing insert which is positioned at the dwell point of the system;

FIG. 14 shows a graph of the internal-external rotation ($\phi_{i-e}$) of the tibia with respect to the femoral component during the deep knee bending simulation of FIG. 13 along with the rotation of the tibial bearing insert with respect to the tibia;

FIG. 15 shows a graph of the results of a deep knee bending simulation using the prior art knee replacement system of FIG. 9 and modified to have an axis of rotation of the tibial bearing insert which is positioned 0.5 inches posterior to the dwell point of the system;

FIG. 16 shows a graph of the internal-external rotation ($\phi_{i-e}$) of the tibia with respect to the femoral component during the deep knee bending simulation of FIG. 15 along with the rotation of the tibial bearing insert with respect to the tibia;

FIG. 29 shows a graph of the results of a deep knee bending simulation using the knee replacement system of FIG. 17 and modified to have an axis of rotation of the tibial bearing insert which is positioned 0.317 inches posterior to the dwell point of the system and 0.317 inches medial to the centerline of the tibial bearing insert;

FIG. 30 shows a graph of the internal-external rotation ($\phi_{i-e}$) of the tibia with respect to the femoral component during the deep knee bending simulation of FIG. 29 along with the rotation of the tibial bearing insert with respect to the tibia;

FIG. 32 depicts a top plan view of the dwell axis and the centerline of the tibial insert of the knee prosthesis of FIG. 31 projected onto the articulating surface of the tibial tray of the knee prosthesis of FIG. 31;

DETAILED DESCRIPTION

Figure 1:
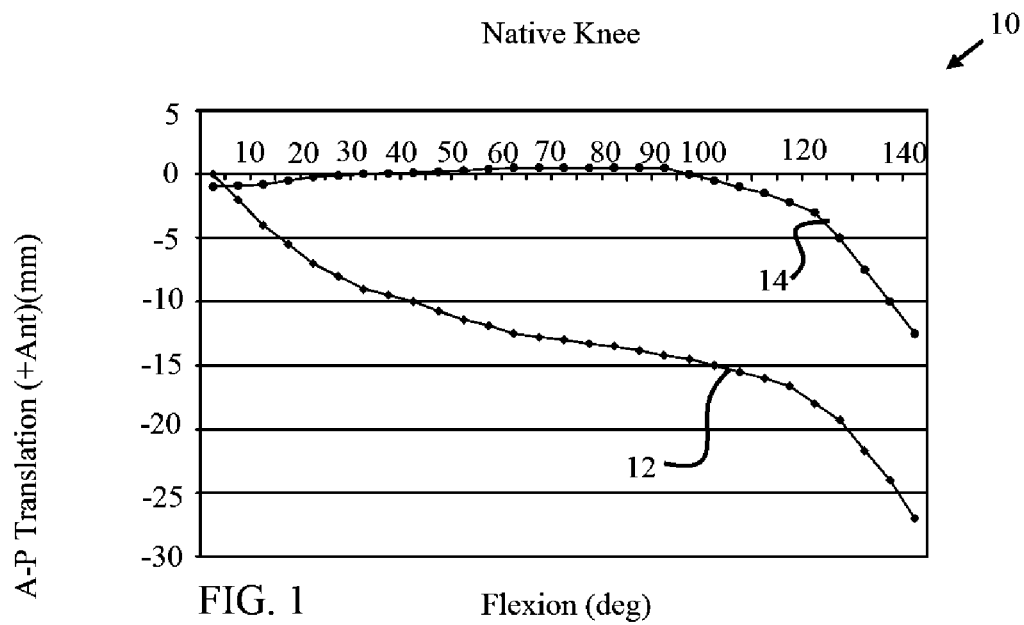
FIG. 1 shows a graph of the reference point locations of the medial and lateral condyle on a tibial component for a native knee during deep knee bending.
Figure 2:
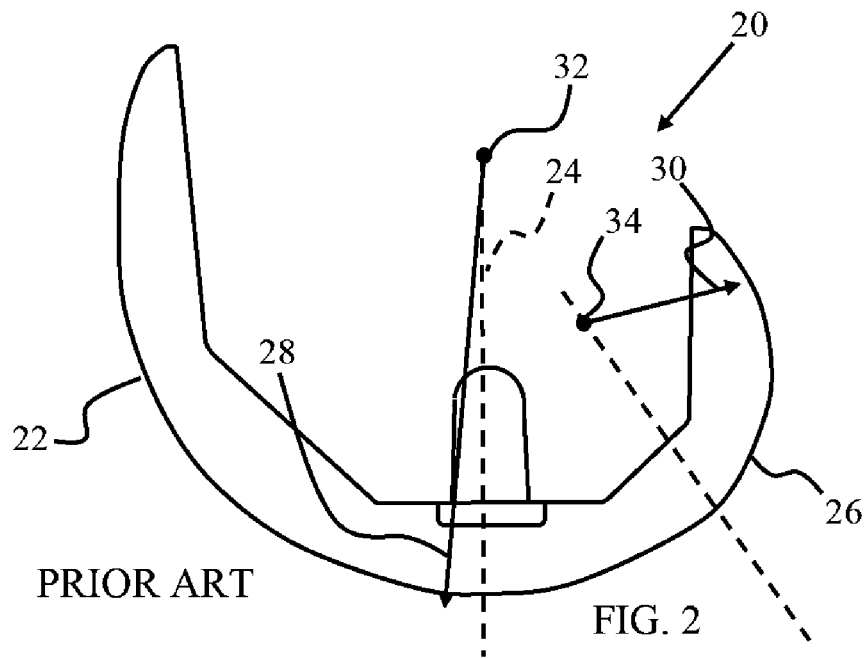
FIG. 2 depicts a sagittal view of a prior art femoral component of a prosthesis with a reduced radius of curvature in the posterior portion of the component.
Figure 3:
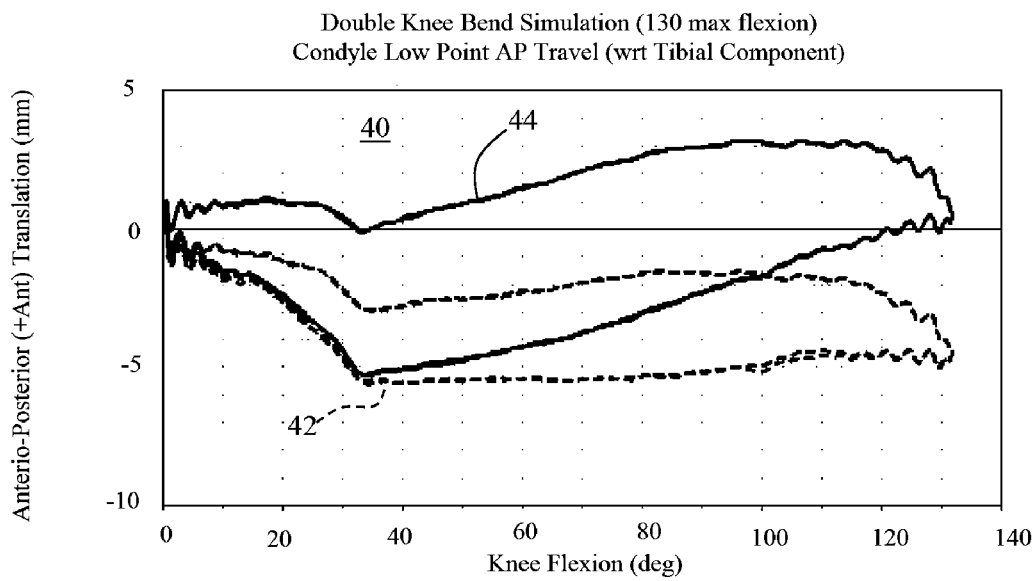
FIG. 3 shows the results of a simulation in the form of a graph of the estimated low (tangency) point locations of the medial and lateral condyles of a femoral component on a tibial component indicating onset of paradoxical anterior translation at about 30 to 35 degrees of flexion.
Figure 4:
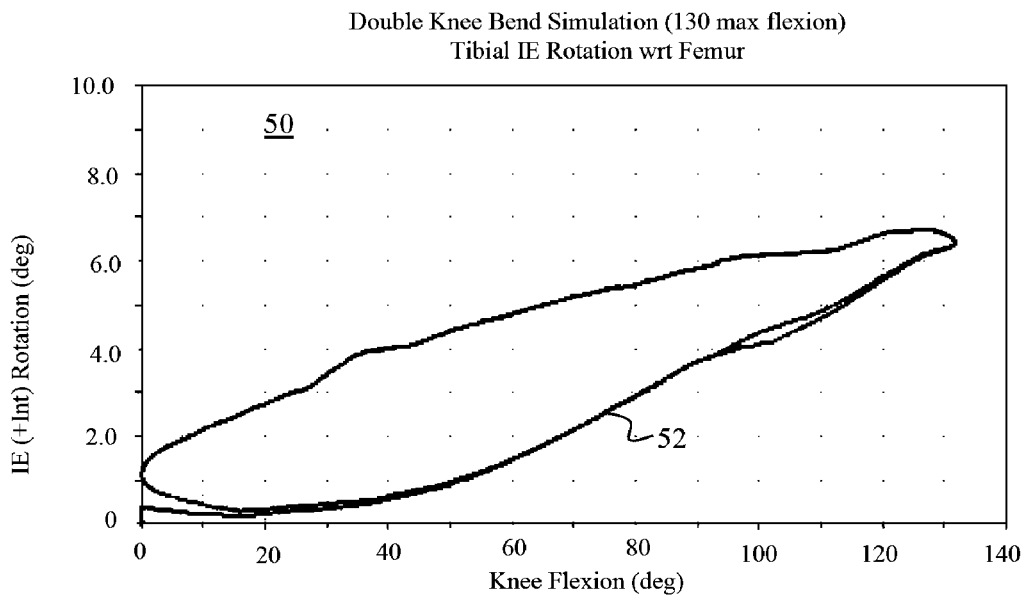
FIG. 4 shows the internal rotation of the tibial component with respect to the femoral component for the simulation of FIG. 3.
Figure 5:
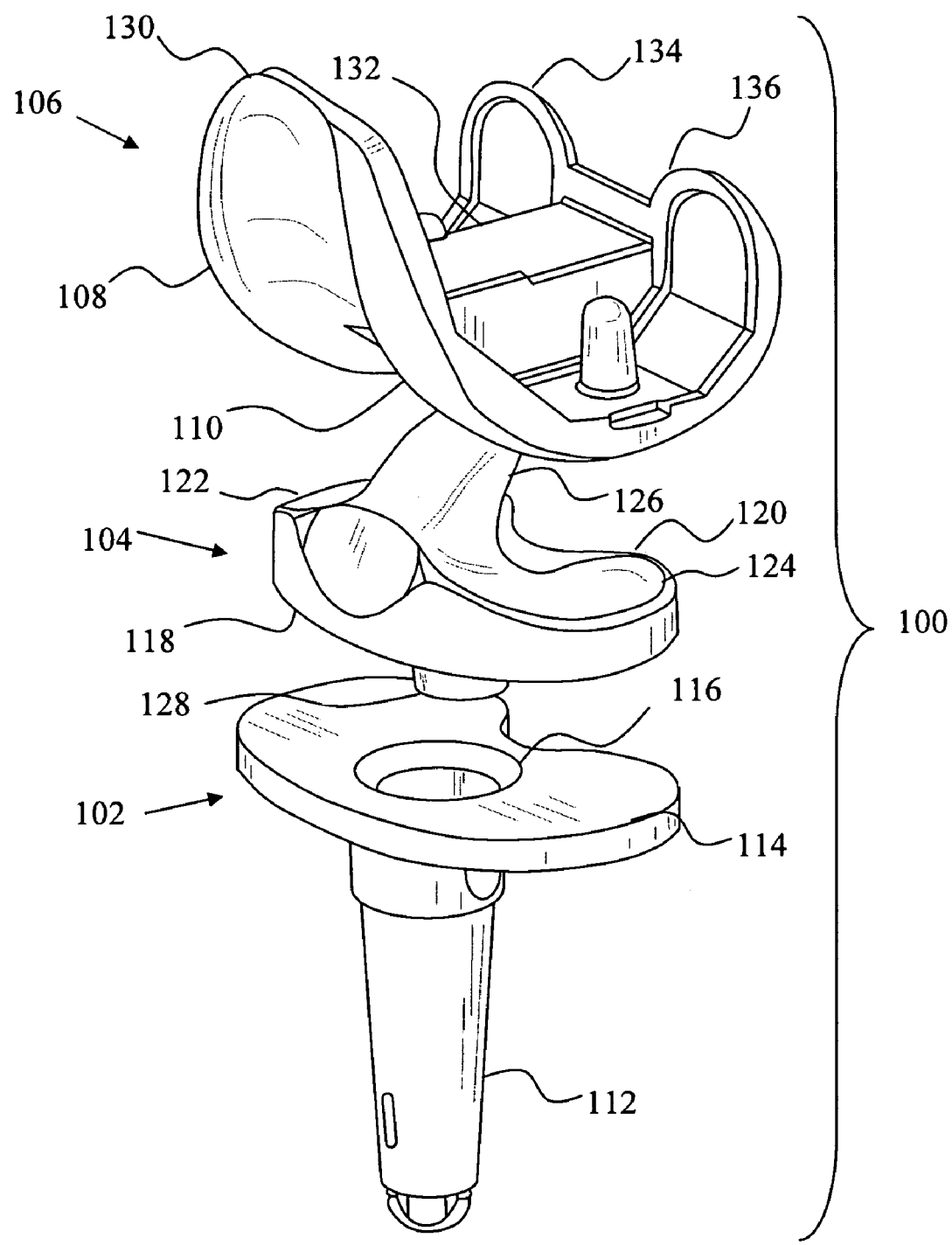
FIG. 5 depicts an exploded perspective view of a prior art knee prosthesis including a femoral component and a tibial component with a rotating plateau having an axis of rotation located anterior to the dwell point.
Figure 10:
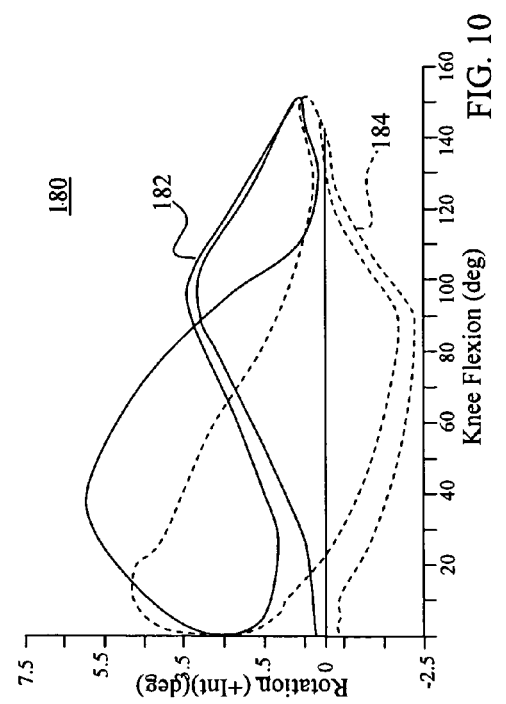
FIG. 10 shows a graph of the internal-external rotation ($\phi_{i-e}$) of the tibia with respect to the femoral component during the deep knee bending simulation of FIG. 9 along with the rotation of the tibial bearing insert with respect to the tibia.

FIG. 5 depicts a knee replacement system 100 incorporating known features. The knee replacement system 100 includes a tibial tray 102, a tibial bearing insert 104 and a femoral component 106 having two femoral condyle elements 108 and 110. The tibial tray 102 includes an inferior stem 112 for attaching the tibial tray 102 to the tibia of a patient and a superior plateau 114 for receiving the tibial bearing insert 104. A coupling member 116 is located on the superior plateau 114.

The tibial bearing insert 104 includes an inferior tibial tray contacting surface 118 and a superior tibial bearing surface 120 The superior tibial bearing surface 120 includes a bearing surface 122 and a bearing surface 124 configured to articulate with the femoral condyle elements 108 and 110. A spine 126 extends upwardly from between the bearing surface 122 and the bearing surface 124. A coupling member 128 extends downwardly from the tibial tray contacting surface 118

The femoral component 106 is configured to be attached to the femur of a patient. A trochlear groove 130 is formed between the femoral condyle elements 108 and 110 which, in this embodiment, are symmetrical. The trochlear groove 130 provides an articulation surface for a patellar component (not shown). A cam compartment 132 is located between posterior portions 134 and 136 of the femoral condyle elements 108 and 110, respectively. Two pegs 138 and 140 are used to mount the femoral component 106 onto the femur of a patient.

FIG. 6 depicts a cross sectional view of the femoral component 106 taken through the cam compartment 132 and a side plan view of the tibial bearing insert 104. An anterior cam 142 and a posterior cam 144 are located within the cam compartment 136. The spine 126 includes an anterior camming portion 146 and a posterior camming portion 148. The anterior cam 142 is configured with the anterior camming portion 146 to preclude undesired posterior slippage when the femoral component 106 is positioned on the tibial bearing insert 104 in extension as shown in FIG. 6.

Figure 34:
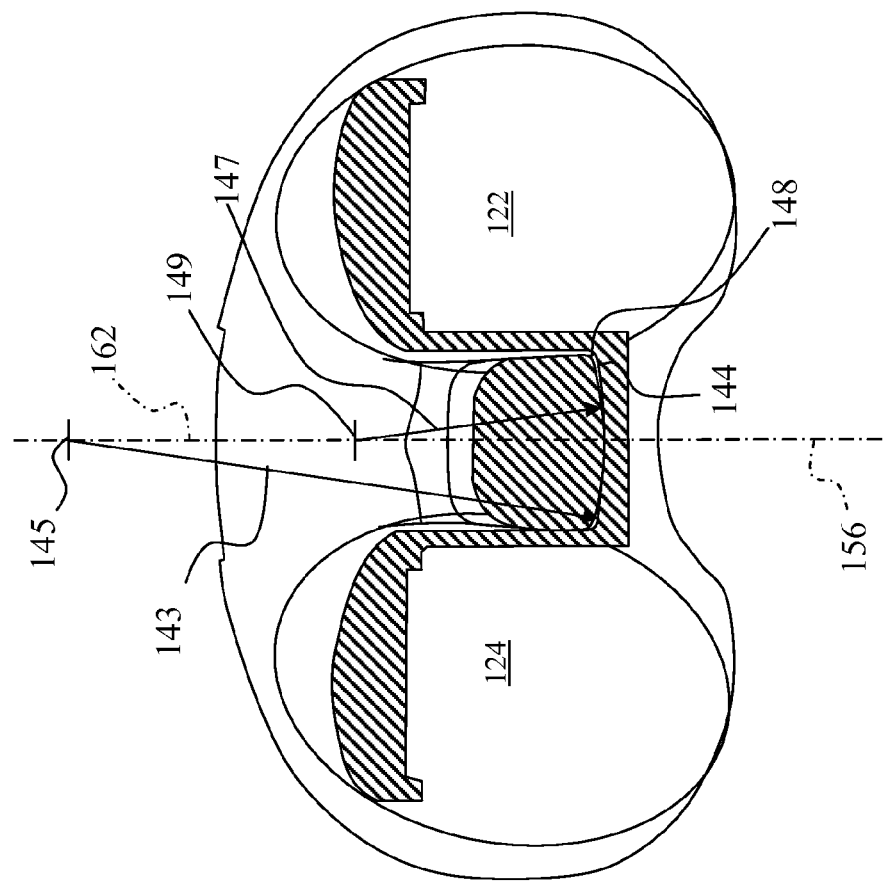
FIG. 34 depicts a medio-lateral cross sectional view of the configuration of FIG. 33 taken along the line A-A of FIG. 33 showing the origins of the radius of curvature of the camming surfaces of the femoral component and the tibial bearing insert to be located on the centerlines of the respective component.
Figure 33:
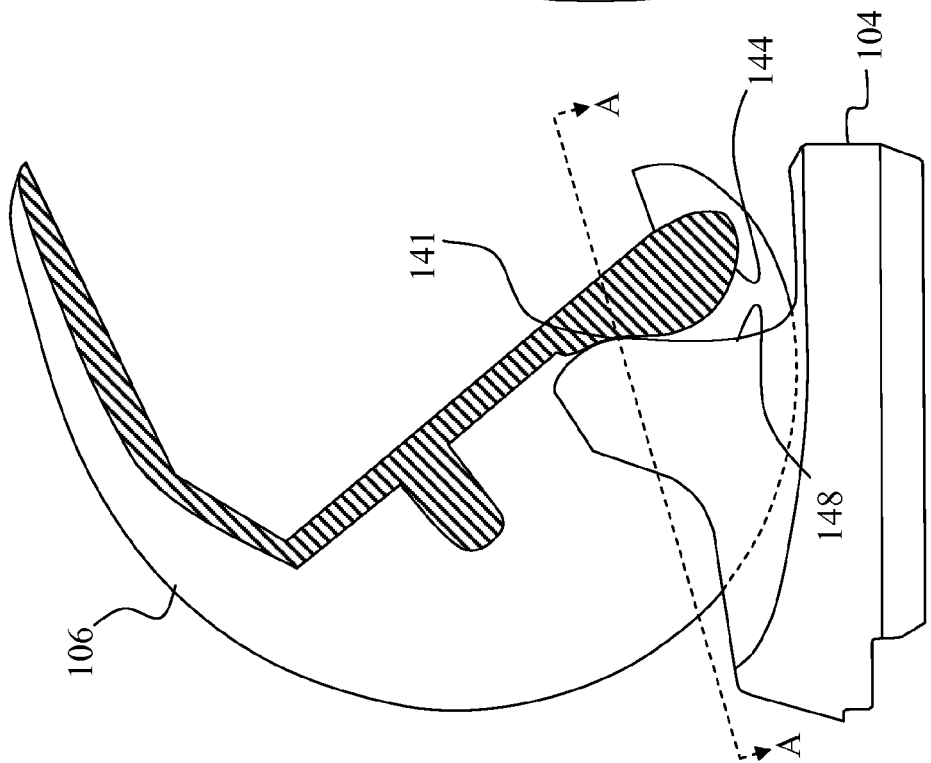
FIG. 33 depicts a sagittal cross sectional view of the femoral component of FIG. 5 and a sagittal plan view of the tibial bearing insert of FIG. 5 showing the contact region between the camming surfaces of the femoral component and the tibial bearing insert with the femoral component positioned at about 70 degrees of flexion on the tibial bearing insert.

With reference to FIG. 33, the femoral component 106 is depicted rotated to about 70 degrees of flexion on the tibial bearing insert 104. At this rotation, the posterior cam 144 and the posterior camming portion 148 are in contact at the contact region 141. FIG. 34 depicts the shape of the posterior camming portion 148 and the shape of the posterior cam 144 at the contact region 141 taken along the line A-A of FIG. 33 which extends from a medial portion of the camming portion 148 and the posterior cam 144 to a lateral portion of the camming portion 148 and the posterior cam 144 in a medio-lateral plane.

The posterior camming portion 148 is formed on a radius of curvature ($R_c$) 147 having an origin 149 on the centerline 156 of the tibial bearing insert 104. In one embodiment, the $R_c$ 147 may be about 20 millimeters. The posterior cam 144 is formed on a radius of curvature ($R_c$) 143 having an origin 145 on the centerline 162 of the femoral component 106. In one embodiment, the $R_c$ 143 may be about 40 millimeters.

The centerline 156 is defined as (i) the straight line extending between the origin 145 of the radius of curvature 143 of the posterior cam 144 and the origin 149 of the radius of curvature 147 of the posterior camming portion 148, (ii) wherein the foregoing origins 145, 149 are the origins for the co-planar radii of curvature 143, 147 of the posterior cam 144 and the posterior camming portion 148 respectively (iii) at a location where the posterior cam 144 and the posterior camming portion 148 initially come into contact during rollback. In the embodiment of FIG. 33, the centerline 156 is thus defined by the origin 149 and the origin 145. The centerline 156 is fixed with respect to the tibial bearing insert 104, that is, if the tibial bearing insert 104 moves or rotates from the orientation depicted in FIG. 34, the centerline 156 moves or rotates as well.

The femoral component 106 is depicted in FIG. 6 in full extension. The low or tangency point of the femoral component 106 is identified as condylar dwell point 150. The condylar dwell point 150 and the condylar dwell point 152 for the condyle element 110, shown projected onto the superior plateau in FIG. 7, define a dwell axis 154. The dwell axis 154 intersects the centerline 156 of the tibial superior bearing surface 120 at a point defined herein as the "dwell point" 158. The dwell point 158 is located posteriorly to the coupling member 116 which, along with the coupling member 128, defines an axis of rotation 160 for the tibial bearing insert 104 (see FIG. 8). The axis of rotation 160 is positioned anteriorly of the dwell point 158.

A deep knee bending simulation was conducted on a prior art device similar to the knee replacement system 100. The prior art device was a NexGen® LPS-flex rotating platform total knee system commercially available from Zimmer, Inc., of Warsaw Indiana. The design parameters of the prior art device that were modeled for the simulation were obtained by reverse engineering. The simulation was conducted using the LifeMOD/KneeSIM version 2007.1.0 Beta 12 and later (LMKS) dynamics program discussed above. The LMKS was configured to model the MCL, and LCL, as well as capsular tissue, as linear springs and the patellar tendon and ligament allowed to wrap around the implants.

Flexion/extension at the hip and ankle joints, and abduction/adduction, varus/valgus and axial rotation at the ankle joint were unconstrained while a constant vertical load of 463 N was applied at the hip. A closed loop controller was used to apply tension to the quadriceps and hamstring muscles to match a prescribed knee-flexion extension profile. The design parameters of the prior art device were imported into the model and subjected to one cycle of deep knee bending up to about 150 degrees of flexion.

The components were positioned so that the dwell point of the insert of the tibio-femoral contact surface lined up in the sagittal plane with the mechanical axis of the leg and the original joint line of the knee was restored. The patellar ligament angle in the sagittal plane at full extension was determined by placing the patellar component at an appropriate supero-inferior position, centered within the trochlear groove of the femoral component and the patellar ligament in the coronal plane was determined by using the default settings of LMKS, which resulted in a Q-angle of about 12 degrees in the coronal plane with the knee at full extension. The rectus femoris coronal angle at full extension was about 7 degrees and the coronal patellar ligament angle at full extension was about 5 degrees fro the vertical mechanical axis of the leg at full extension.

The results of the above defined modeling scenario, hereinafter referred to as "the LMKS Modeling Results, included the anterior-posterior positions of the lowest points on the femoral lateral and medial condyles closest to the tibial tray which were recorded relative to the dwell points. Additionally, rotation of the tibia relative to the femur and rotation of the tibial insert relative to the tibial tray was reported using the Grood & Suntay coordinate system. In discussions of the LMKS Modeling Results for the prior art device shown in FIGS. 9-16, the reference numbers for the corresponding component of the knee replacement system 100 will be referenced, with the condyle 108 designated as the medial condyle and the condyle 110 designated as the lateral condyle.

Figure 9:
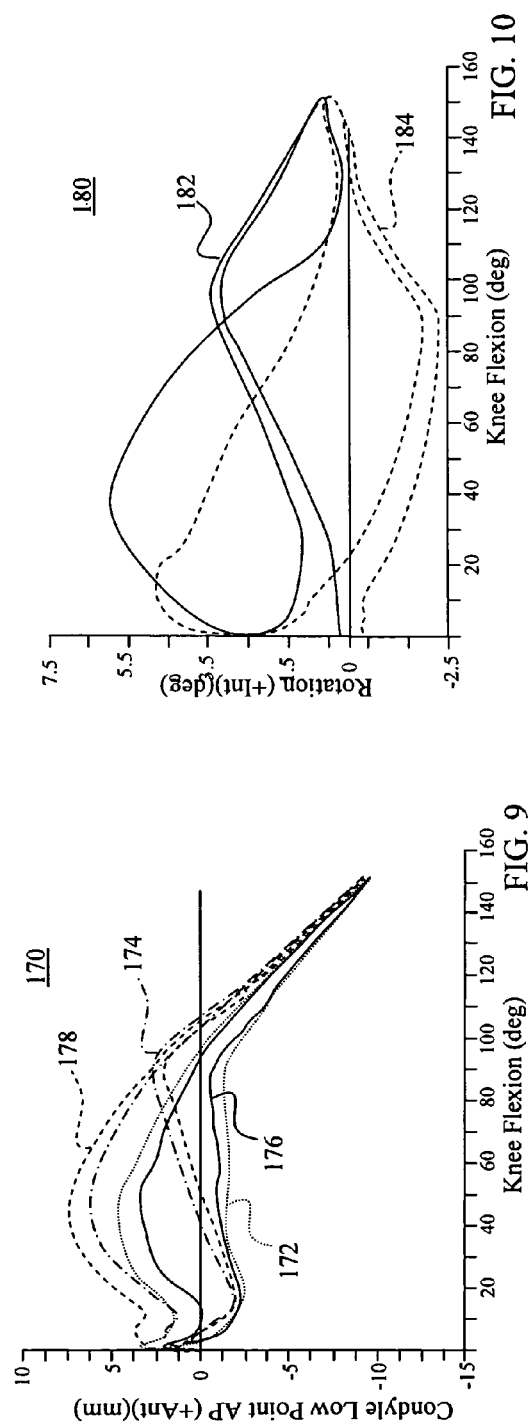
FIG. 9 shows a graph of the results of a deep knee bending simulation using a prior art knee replacement system modeled from reverse engineered data.

LMKS Modeling Results for the simulation of the femoral component 106 on the tibial bearing insert 104 are shown in FIG. 9 wherein the graph 170 includes lines 172 and 174 which show the estimated low (tangency) points for the lateral condylar surface 110 and the medial condylar surface 108, respectively, of the femoral component 106 on the tibial bearing insert 104. The graph 170 further includes lines 176 and 178 which show the estimated low (tangency) points for the lateral condylar surface 110 and the medial condylar surface 108, respectively, of the femoral component 106 with respect to the tibial tray 102. The lower portion of the lines 172, 174, 176 and 178 were generated as the components were moving into flexion.

The graph 170 generally shows the femoral component 106 is moving posteriorly or "rolling back" on the tibial bearing insert 104 until about 20 degrees of flexion and again from about 90 degrees of flexion to 150 degrees of flexion. The amount of rollback of the lateral condylar surface 110 and the medial condylar surface 108 is not the same. This difference indicates that the femoral component 106 is rotating. This conclusion is supported by the LMKS Modeling Results for the femoral component 106 on the tibial bearing insert 104 shown in the graph 180 of FIG. 10 wherein the line 182 of the graph 180 identifies the $\phi_{i-e}$ of the femoral component 106 with respect to the tibia. The line 182 reveals that between 0 degrees of flexion and about 100 degrees of flexion, the $\phi_{i-e}$ for the femoral component 106 with respect to the tibia is steadily increasing to about 3.5 degrees.

The graph 180 further includes a line 184 which identifies the rotation of the tibial bearing insert 104 with respect to the tibia. The line 184, in contrast to the line 182, reveals that between 0 degrees of flexion and about 90 degrees of flexion, the rotation for the tibial bearing insert 104 with respect to the tibia is steadily decreasing to about −2.5 degrees, indicating a maximum difference in rotation between the femoral component 106 and the tibial bearing insert 104 of about 5 degrees between about 90 and about 110 degrees of flexion.

Figure 11:
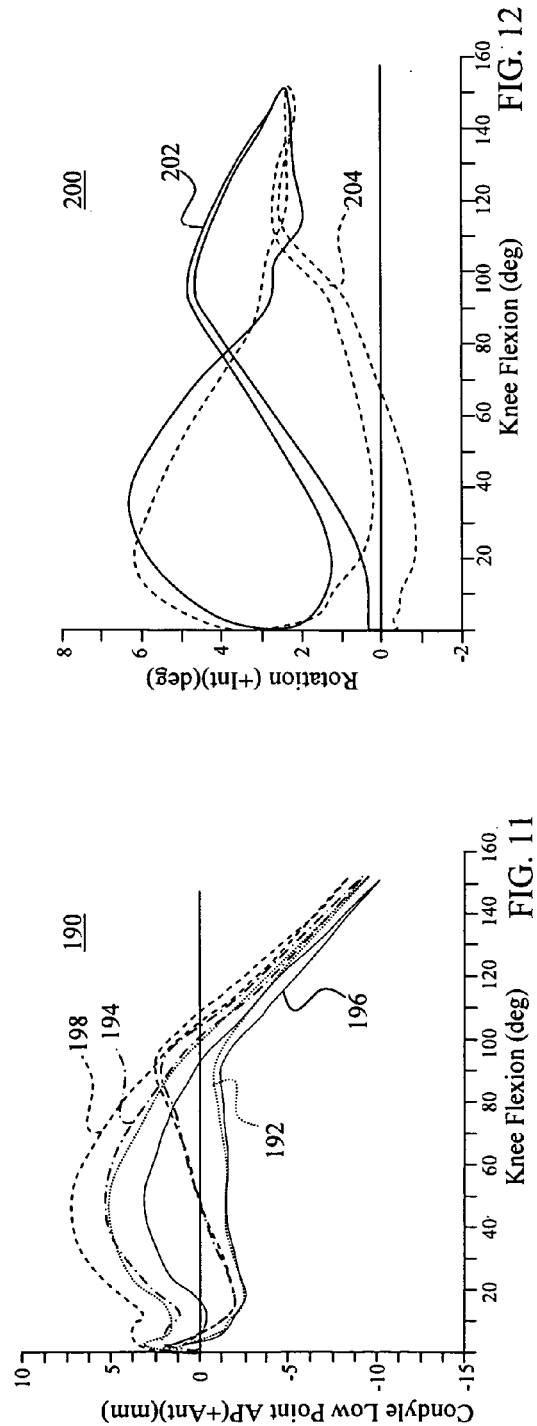
FIG. 11 shows a graph of the results of a deep knee bending simulation using the prior art knee replacement system of FIG. 9 and modified to have an axis of rotation of the tibial bearing insert which is positioned at 0.2 inches anterior to the dwell point of the system.

Reverse engineering of the prior art system used in the foregoing modeling scenario indicates that the axis of rotation 160 of the tibial bearing insert 104 of the prior art device was located 0.5 inches anterior to the dwell point 158 (the "0.5A configuration"). The model of the prior art device was then modified to place the axis of rotation 160 of the tibial bearing insert 104 at 0.2 inches anterior to the dwell point 158 (the "0.2A configuration"). LMKS Modeling Results for the 0.2A configuration are shown in FIG. 11 wherein the graph 190 includes lines 192 and 194 which show the estimated low (tangency) points for the lateral condylar surface 110 and the medial condylar surface 108, respectively, of the femoral component 106 on the tibial bearing insert 104. The graph 190 further includes lines 196 and 198 which show the estimated low (tangency) points for the lateral condylar surface 110 and the medial condylar surface 108, respectively, of the femoral component 106 with respect to the tibial tray 102. The lower portion of the lines 192, 194, 196, and 198 were generated as the components were moving into flexion.

The graph 190 generally shows the femoral component 106 is moving posteriorly or "rolling back" on the tibial bearing insert 104 until about 20 degrees of flexion and again from about 90 degrees of flexion to 150 degrees of flexion. The rollback exhibited with the 0.2A configuration is substantially the same as the rollback exhibited in the 0.5A configuration.

Figure 12:
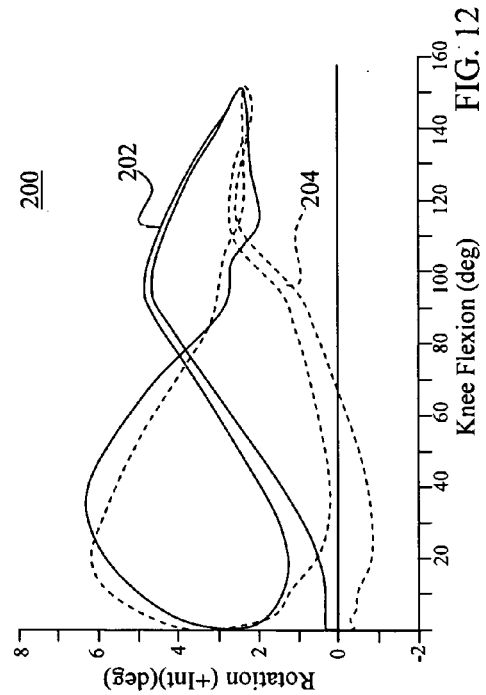
FIG. 12 shows a graph of the internal-external rotation ($\phi_{i-e}$) of the tibia with respect to the femoral component during the deep knee bending simulation of FIG. 11 along with the rotation of the tibial bearing insert with respect to the tibia.

The graph 200 of FIG. 12 includes the line 202 which identifies the $\phi_{i-e}$ of the femoral component 106 with respect to the tibia. The line 202 reveals that between 0 degrees of flexion and about 100 degrees of flexion, the $\phi_{i-e}$ for the femoral component 106 with respect to the tibia is steadily increasing to over 4 degrees. The graph 200 further includes a line 204 which identifies the rotation of the tibial bearing insert 104 with respect to the tibia. The line 204 reveals that between 0 degrees of flexion and about 20 degrees of flexion, there is a slight decrease in the rotation of the tibial bearing insert 104 with respect to the tibia, followed by a steady increase through about 120 degrees of flexion. Thus, the maximum difference in rotation between the femoral component 106 and the tibial bearing insert 104 is reduced to less than 4 degrees at about 90 degrees of flexion.

The model of the prior art device was then modified to place the axis of rotation 160 of the tibial bearing insert 104 at the dwell point 158 (the "0.0 configuration"). LMKS Modeling Results for the 0.0A configuration are shown in FIG. 13 wherein the graph 210 includes lines 212 and 214 which show the estimated low (tangency) points for the lateral condylar surface 110 and the medial condylar surface 108, respectively, of the femoral component 106 on the tibial bearing insert 104. The graph 210 further includes lines 216 and 218 which show the estimated low (tangency) points for the lateral condylar surface 110 and the medial condylar surface 108, respectively, of the femoral component 106 with respect to the tibial tray 102. The lower portion of the lines 212, 214, 216 and 218 were generated as the components were moving into flexion.

The graph 210 generally shows the femoral component 106 is moving posteriorly or "rolling back" on the tibial bearing insert 104 until about 20 degrees of flexion and again from about 90 degrees of flexion to 150 degrees of flexion. The rollback exhibited with the 0.0 configuration is substantially the same as the rollback exhibited in the 0.5A configuration.

The graph 220 of FIG. 14 includes the line 222 which identifies the $\phi_{i-e}$ of the femoral component 106 with respect to the tibia. The line 222 reveals that between 0 degrees of flexion and about 100 degrees of flexion, the $\phi_{i-e}$ for the femoral component 106 with respect to the tibia is steadily increasing to almost 5 degrees. The graph 220 further includes a line 224 which identifies the rotation of the tibial bearing insert 104 with respect to the tibia. The line 224 reveals that between 0 degrees of flexion and about 20 degrees of flexion, there is a slight decrease in the rotation of the tibial bearing insert 104 with respect to the tibia, followed by a steady increase through about 120 degrees of flexion. Thus, the maximum difference in rotation between the femoral component 106 and the tibial bearing insert 104 is reduced to less than 2.5 degrees at about 90 degrees of flexion. On subsequent cycles, the maximum difference in rotation remains about the same, but the line 224 conforms more closely to the line 222.

The model of the prior art device was then modified to place the axis of rotation 160 of the tibial bearing insert 104 at 0.5 inches posterior to the dwell point 158 (the "0.5P configuration"). LMKS Modeling Results for the 0.5P configuration are shown in FIG. 15 wherein the graph 230 includes lines 232 and 234 which show the estimated low (tangency) points for the lateral condylar surface 110 and the medial condylar surface 108, respectively, of the femoral component 106 on the tibial bearing insert 104. The graph 230 further includes lines 236 and 238 which show the estimated low (tangency) points for the lateral condylar surface 110 and the medial condylar surface 108, respectively, of the femoral component 106 with respect to the tibial tray 102. The lower portion of the lines 232, 234, 236, and 238 were generated as the components were moving into flexion.

The graph 230 generally shows the femoral component 106 is moving posteriorly or "rolling back" on the tibial bearing insert 104 until about 20 degrees of flexion and again from about 90 degrees of flexion to 150 degrees of flexion. The rollback exhibited with the 0.5P configuration is substantially the same as the rollback exhibited in the 0.5A configuration.

The graph 240 of FIG. 16 includes the line 242 which identifies the $\phi_{i-e}$ of the femoral component 106 with respect to the tibia. The line 242 reveals that between 0 degrees of flexion and about 100 degrees of flexion, the $\phi_{i-e}$ for the femoral component 106 with respect to the tibia is steadily increasing to almost 6 degrees. The graph 240 further includes a line 244 which identifies the rotation of the tibial bearing insert 104 with respect to the tibia. The line 244 reveals that between 0 degrees of flexion and about 10 degrees of flexion, there is a slight decrease in the rotation of the tibial bearing insert 104 with respect to the tibia, followed by a steady increase through about 120 degrees of flexion. Thus, the maximum difference in rotation between the femoral component 106 and the tibial bearing insert 104 is reduced to just over 1 degree at about 95 degrees of flexion. On subsequent cycles, the line 244 conforms very closely with the line 242. The excursion of the line 244 above the line 242 as the joint travels toward a flexed position in the 0.5P configuration is somewhat larger than the excursion of the line 224 above the line 222 in the 0.0 configuration.

The FIGS. 9-16 thus show that as the axis of rotation 160 is moved posteriorly, increased fidelity between the rotation of the femoral component 106 with respect to the tibial tray 102 and the rotation of the tibial bearing insert 104 with respect to the tibial tray 102 is realized. Additionally, the $\phi_{i-e}$ for the femoral component 106 with respect to the tibia more than doubles.

Validation of the principles set forth herein was accomplished by a series of additional modeling scenarios using a differently configured knee replacement system. In discussions of the LMKS Modeling Results for the differently configured device shown in FIGS. 17-30, the reference numbers for the corresponding component of the knee replacement system 100 will be referenced.

Figure 17:
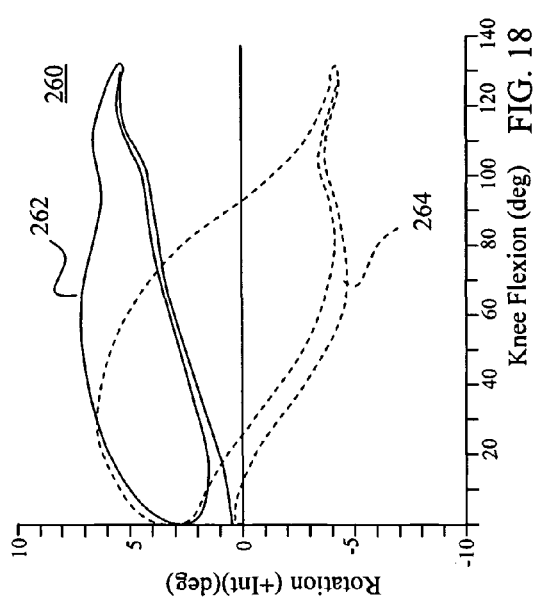
FIG. 17 shows a graph of the results of a deep knee bending simulation using a knee replacement system different from the prior art knee replacement system of FIG. 9 and modified to have an axis of rotation of the tibial bearing insert which is positioned at 0.317 inches anterior to the dwell point of the system.

The model of the differently configured device was established with the axis of rotation 160 of the tibial bearing insert 104 at the centerline 156 and 0.317 inches anterior to the dwell point 158 (the "0/0.317A configuration"). LMKS Modeling Results for the 0/0.317A configuration are shown in FIG. 17 wherein the graph 250 includes lines 252 and 254 which show the estimated low (tangency) points for the lateral condylar surface 110 and the medial condylar surface 108, respectively, of the femoral component 106 on the tibial bearing insert 104. The graph 250 further includes lines 256 and 258 which show the estimated low (tangency) points for the lateral condylar surface 110 and the medial condylar surface 108, respectively, of the femoral component 106 with respect to the tibial tray 102. The lower portion of the lines 252, 254, 256, and 258 were generated as the components were moving into flexion.

The graph 250 generally shows the femoral component 106 is moving posteriorly or "rolling back" on the tibial bearing insert 104 until about 30 degrees of flexion and again from about 105 degrees of flexion to 130 degrees of flexion.

Figure 18:
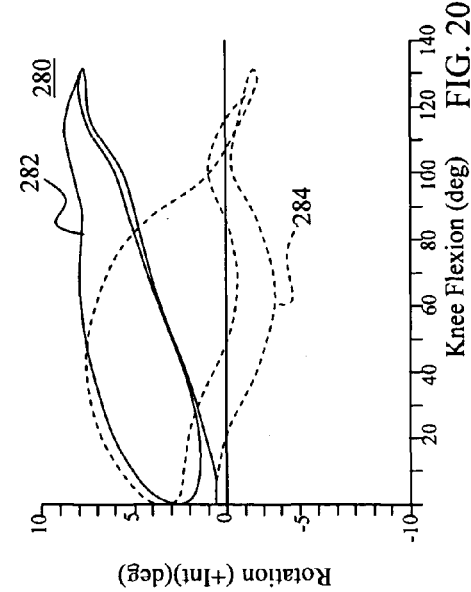
FIG. 18 shows a graph of the internal-external rotation ($\phi_{i-e}$) of the tibia with respect to the femoral component during the deep knee bending simulation of FIG. 17 along with the rotation of the tibial bearing insert with respect to the tibia.

The graph 260 of FIG. 18 includes the line 262 which identifies the $\phi_{i-e}$ of the femoral component 106 with respect to the tibia. The line 262 reveals that between 0 degrees of flexion and about 120 degrees of flexion, the $\phi_{i-e}$ for the femoral component 106 with respect to the tibia is steadily increasing to just over 5 degrees. The graph 260 further includes a line 264 which identifies the rotation of the tibial bearing insert 104 with respect to the tibia. The line 264 reveals that between 0 degrees of flexion and about 70 degrees of flexion, there is a steady decrease in the rotation of the tibial bearing insert 104 with respect to the tibia, followed by a relatively constant rotation angle through about 130 degrees of flexion. Thus, the maximum difference in rotation between the femoral component 106 and the tibial bearing insert 104 constantly increases to about 10 degrees at about 120 degrees of flexion. The maximum difference was about 10 degrees on subsequent cycles.

Figure 19:
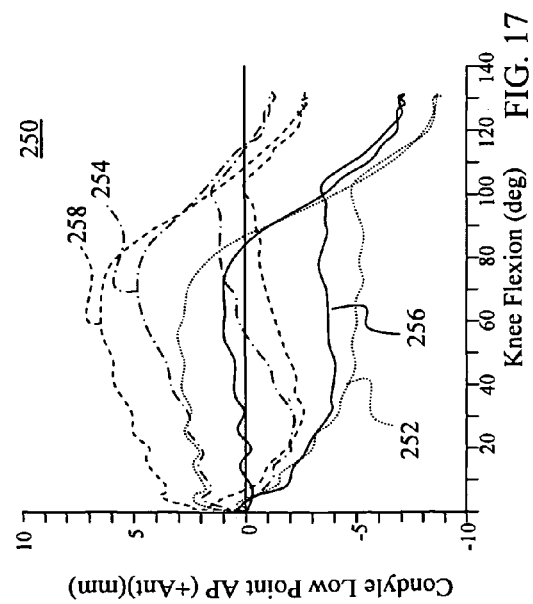
FIG. 19 shows a graph of the results of a deep knee bending simulation using the knee replacement system of FIG. 17 and modified to have an axis of rotation of the tibial bearing insert which is positioned at the dwell point of the system.

The model of the differently configured device was then modified to place the axis of rotation 160 of the tibial bearing insert 104 on the centerline 156 at the dwell point 158 (the "0/0 configuration"). LMKS Modeling Results for the 0/0 configuration are shown in FIG. 19 wherein the graph 270 includes lines 272 and 274 which show the estimated low (tangency) points for the lateral condylar surface 110 and the medial condylar surface 108, respectively, of the femoral component 106 on the tibial bearing insert 104. The graph 270 further includes lines 276 and 278 which show the estimated low (tangency) points for the lateral condylar surface 110 and the medial condylar surface 108, respectively, of the femoral component 106 with respect to the tibial tray 102. The lower portion of the lines 272, 274, 276, and 278 were generated as the components were moving into flexion.

The graph 270 generally shows the femoral component 106 is moving posteriorly or "rolling back" on the tibial bearing insert 104 until about 30 degrees of flexion and again from about 95 degrees of flexion to 130 degrees of flexion. The rollback exhibited with the 0/0 configuration is substantially the same as the rollback exhibited in the 0/0.317A configuration, although the second rollback event occurred at an earlier flexion angle.

Figure 20:
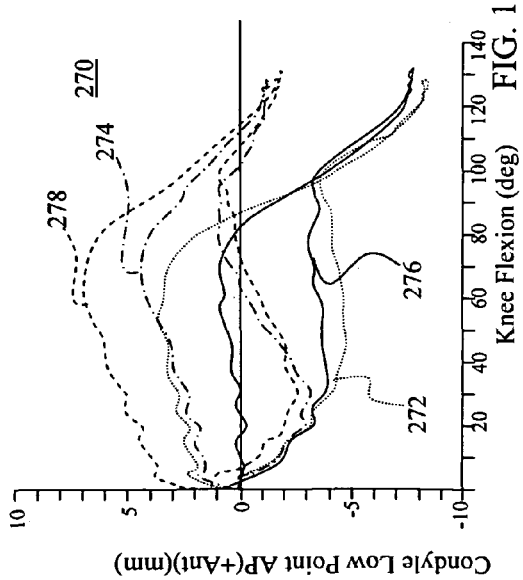
FIG. 20 shows a graph of the internal-external rotation ($\phi_{i-e}$) of the tibia with respect to the femoral component during the deep knee bending simulation of FIG. 19 along with the rotation of the tibial bearing insert with respect to the tibia.

The graph 280 of FIG. 20 includes the line 282 which identifies the $\phi_{i-e}$ of the femoral component 106 with respect to the tibia. The line 282 reveals that between 0 degrees of flexion and about 130 degrees of flexion, the $\phi_{i-e}$ for the femoral component 106 with respect to the tibia is steadily increasing to over 7 degrees. The graph 280 further includes a line 284 which identifies the rotation of the tibial bearing insert 104 with respect to the tibia. The line 284 reveals that between 0 degrees of flexion and about 65 degrees of flexion, there is a steady decrease in the rotation of the tibial bearing insert 104 with respect to the tibia, followed by a steady increase through about 105 degrees of flexion. Thus, the maximum difference in rotation between the femoral component 106 and the tibial bearing insert 104 is reduced to about 8 degrees at about 65 degrees of flexion and slightly more than 8 degrees at about 130 degrees of flexion. On subsequent cycles, the maximum difference at 65 degrees was reduced to about 5 degrees while the maximum difference at 130 remained at slightly more than 8 degrees.

Figure 21:
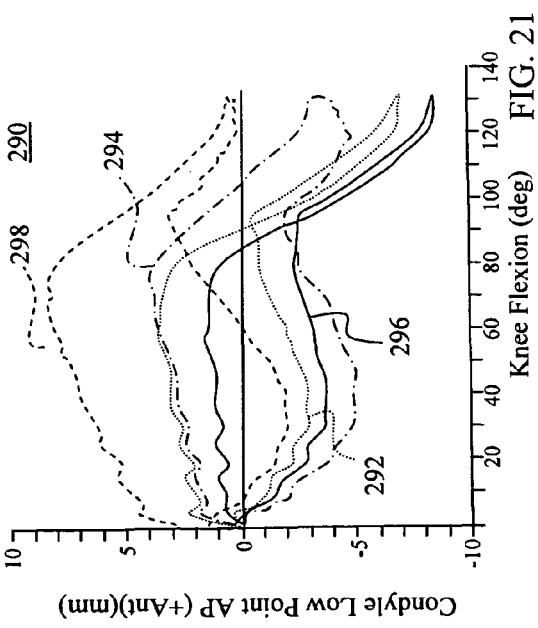
FIG. 21 shows a graph of the results of a deep knee bending simulation using the knee replacement system of FIG. 17 and modified to have an axis of rotation of the tibial bearing insert which is positioned 0.317 inches lateral to the dwell point of the system.

The model of the differently configured device was then modified to place the axis of rotation 160 of the tibial bearing insert 104 at 0.317 inches lateral of the centerline 156 and on the dwell axis 154 (the "0.317L/0 configuration"). LMKS Modeling Results for the 0.317L/0 configuration are shown in FIG. 21 wherein the graph 290 includes lines 292 and 294 which show the estimated low (tangency) points for the lateral condylar surface 110 and the medial condylar surface 108, respectively, of the femoral component 106 on the tibial bearing insert 104. The graph 290 further includes lines 296 and 298 which show the estimated low (tangency) points for the lateral condylar surface 110 and the medial condylar surface 108, respectively, of the femoral component 106 with respect to the tibial tray 102. The lower portion of the lines 292, 294, 296, and 298 were generated as the components were moving into flexion.

The graph 290 generally shows the femoral component 106 is moving posteriorly or "rolling back" on the tibial bearing insert 104 until just over 30 degrees of flexion and again from about 95 degrees of flexion to 130 degrees of flexion. The rollback exhibited with the 0.317L/0 configuration is similar to the rollback exhibited in the 0/0.317A configuration.

Figure 22:
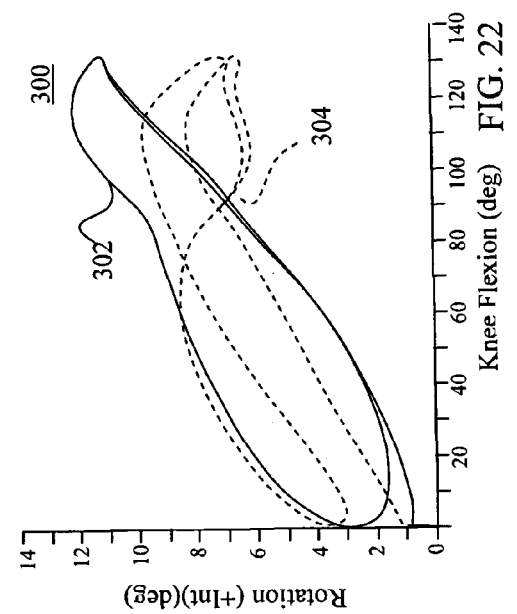
FIG. 22 shows a graph of the internal-external rotation ($\phi_{i-e}$) of the tibia with respect to the femoral component during the deep knee bending simulation of FIG. 21 along with the rotation of the tibial bearing insert with respect to the tibia.

The graph 300 of FIG. 22 includes the line 302 which identifies the $\phi_{i-e}$ of the femoral component 106 with respect to the tibia. The line 302 reveals that between 0 degrees of flexion and about 130 degrees of flexion, the $\phi_{i-e}$ for the femoral component 106 with respect to the tibia is steadily increasing to over 11 degrees. The graph 300 further includes a line 304 which identifies the rotation of the tibial bearing insert 104 with respect to the tibia. The line 304 reveals that between 0 degrees of flexion and about 110 degrees of flexion, there is a steady increase in the rotation of the tibial bearing insert 104 with respect to the tibia to about 8 degrees, followed by a drop to about 7 degrees of rotation at 130 degrees of flexion. Thus, the rotation of the tibial bearing insert 104 with respect to the tibia is slightly greater than or equal to the $\phi_{i-e}$ for the femoral component 106 through about 100 degrees of flexion with a maximum difference in rotation between the femoral component 106 and the tibial bearing insert 104 of just over 5 degrees at 130 degrees of flexion. On subsequent cycles, the maximum difference in rotation of the tibial bearing insert 104 with respect to the tibia is slightly increased, pushing the crossover point to about 115 degrees of flexion with a maximum difference in rotation between the femoral component 106 and the tibial bearing insert 104 of about 4 degrees at 130 degrees of flexion.

Figure 23:
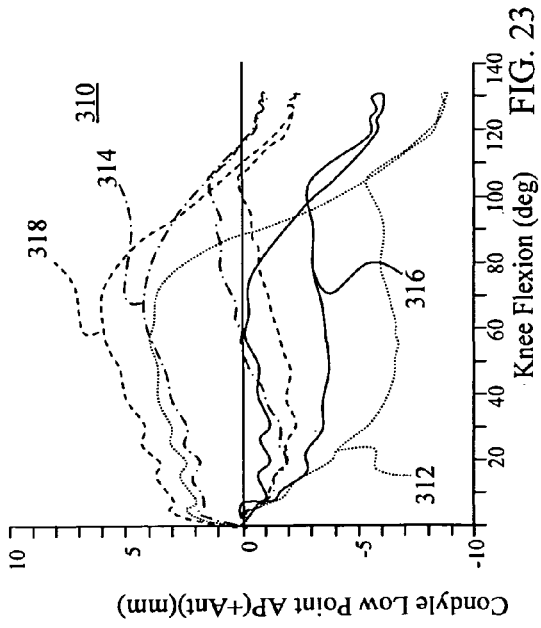
FIG. 23 shows a graph of the results of a deep knee bending simulation using the knee replacement system of FIG. 17 and modified to have an axis of rotation of the tibial bearing insert which is positioned 0.317 inches medial to the dwell point of the system.

The model of the differently configured device was then modified to place the axis of rotation 160 of the tibial bearing insert 104 at 0.317 inches medial of the centerline 156 and on the dwell axis 154 (the "0.317M/0 configuration"). LMKS Modeling Results for the 0.317M/0 configuration are shown in FIG. 23 wherein the graph 310 includes lines 312 and 314 which show the estimated low (tangency) points for the lateral condylar surface 110 and the medial condylar surface 108, respectively, of the femoral component 106 on the tibial bearing insert 104. The graph 310 further includes lines 316 and 318 which show the estimated low (tangency) points for the lateral condylar surface 110 and the medial condylar surface 108, respectively, of the femoral component 106 with respect to the tibial tray 102. The lower portion of the lines 312, 314, 316, and 318 were generated as the components were moving into flexion.

The graph 310 generally shows the lateral condyle element 110 of the femoral component 106 is moving posteriorly or "rolling back" on the tibial bearing insert 104 until about 65 degrees of flexion while the medial condyle 108 exhibits rollback to about 35 degrees of flexion. The femoral component 106 exhibits additional rollback from about 105 degrees of flexion to 130 degrees of flexion.

Figure 24:
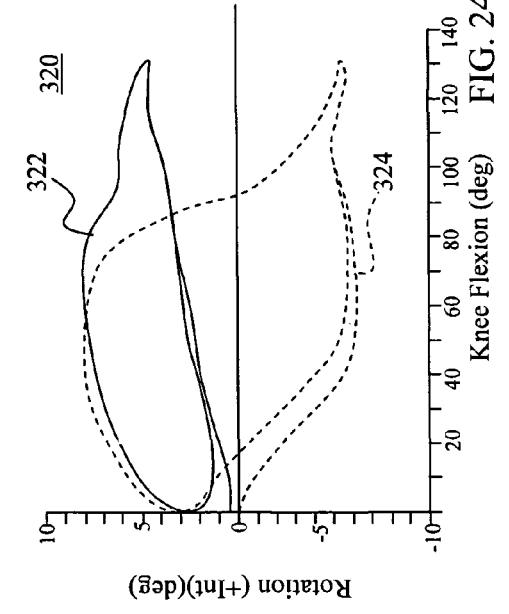
FIG. 24 shows a graph of the internal-external rotation ($\phi_{i-e}$) of the tibia with respect to the femoral component during the deep knee bending simulation of FIG. 23 along with the rotation of the tibial bearing insert with respect to the tibia.

The graph 320 of FIG. 24 includes the line 322 which identifies the $\phi_{i\text{-}e}$ of the femoral component 106 with respect to the tibia. The line 322 reveals that between 0 degrees of flexion and about 115 degrees of flexion, the $\phi_{i\text{-}e}$ for the femoral component 106 with respect to the tibia is steadily increasing to just under 5 degrees. The graph 320 further includes a line 324 which identifies the rotation of the tibial bearing insert 104 with respect to the tibia. The line 324 reveals that between 0 degrees of flexion and about 50 degrees of flexion, there is a steady decrease in the rotation of the tibial bearing insert 104 with respect to the tibia, followed by a relatively constant rotation of about −5 degrees through about 130 degrees of flexion. Thus, the maximum difference in rotation between the femoral component 106 and the tibial bearing insert 104 is about 11 degrees at about 130 degrees of flexion. On subsequent cycles, the maximum difference in rotation was also about 11 degrees.

Figure 25:
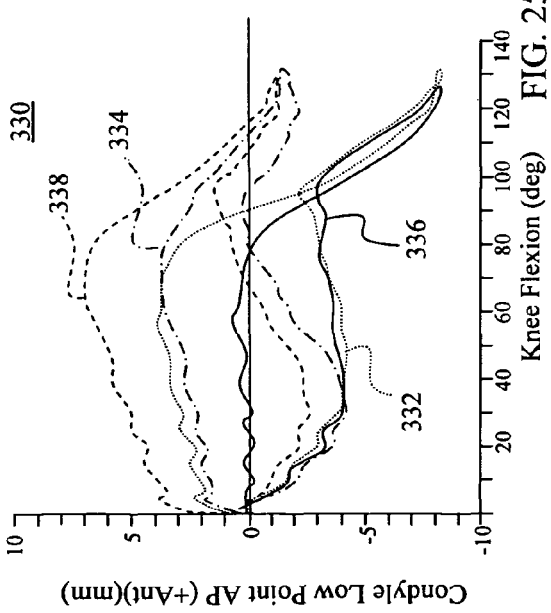
FIG. 25 shows a graph of the results of a deep knee bending simulation using the knee replacement system of FIG. 17 and modified to have an axis of rotation of the tibial bearing insert which is positioned 0.317 inches posterior to the dwell point of the system.

The model of the differently configured device was then modified with the axis of rotation 160 of the tibial bearing insert 104 on the centerline 156 and 0.317 inches posterior to the dwell axis 154 (the "0/0.317P configuration"). LMKS Modeling Results for the 0/0.317P configuration are shown in FIG. 25 wherein the graph 330 includes lines 332 and 334 which show the estimated low (tangency) points for the lateral condylar surface 110 and the medial condylar surface 108, respectively, of the femoral component 106 on the tibial bearing insert 104. The graph 330 further includes lines 336 and 338 which show the estimated low (tangency) points for the lateral condylar surface 110 and the medial condylar surface 108, respectively, of the femoral component 106 with respect to the tibial tray 102. The lower portion of the lines 332, 334, 336, and 338 were generated as the components were moving into flexion.

The graph 330 generally shows the femoral component 106 is moving posteriorly or "rolling back" on the tibial bearing insert 104 until about 35 degrees of flexion and again from about 95 degrees of flexion to 130 degrees of flexion.

Figure 26:
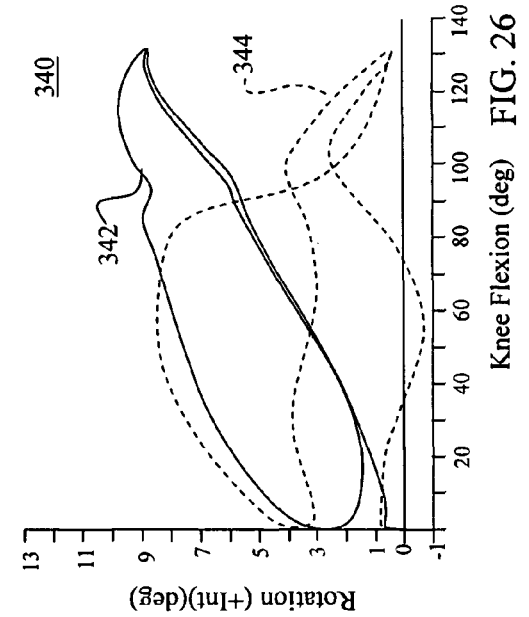
FIG. 26 shows a graph of the internal-external rotation ($\phi_{i-e}$) of the tibia with respect to the femoral component during the deep knee bending simulation of FIG. 25 along with the rotation of the tibial bearing insert with respect to the tibia.

The graph 340 of FIG. 26 includes the line 342 which identifies the $\phi_{i\text{-}e}$ of the femoral component 106 with respect to the tibia. The line 342 reveals that between 0 degrees of flexion and about 130 degrees of flexion, the $\phi_{i\text{-}e}$ for the femoral component 106 with respect to the tibia is steadily increasing to almost 9 degrees. The graph 340 further includes a line 344 which identifies the rotation of the tibial bearing insert 104 with respect to the tibia. The line 344 reveals that between 0 degrees of flexion and about 55 degrees of flexion, there is a slight decrease in the rotation of the tibial bearing insert 104 with respect to the tibia, followed by a steady increase through about 105 degrees of flexion followed by a steady decrease in rotation. Thus, the maximum difference in rotation between the femoral component 106 and the tibial bearing insert 104 is about 9 degrees at about 130 degrees of flexion. On subsequent cycles, the rotation of the tibial bearing insert 104 with respect to the tibia remained at about 3 degrees of rotation until about 100 degrees of flexion at which point the rotation angle decreased to about zero degrees. Thus, the maximum difference in rotation between the femoral component 106 and the tibial bearing insert 104 was about 9 degrees at about 130 degrees of flexion for the subsequent cycles.

Figure 27:
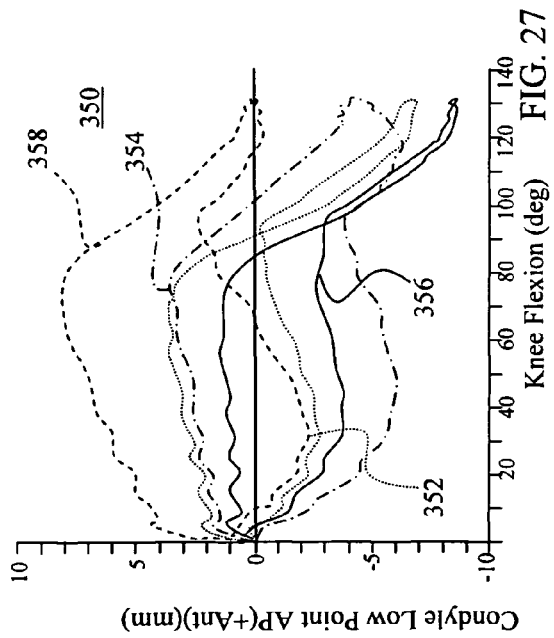
FIG. 27 shows a graph of the results of a deep knee bending simulation using the knee replacement system of FIG. 17 and modified to have an axis of rotation of the tibial bearing insert which is positioned 0.317 inches posterior to the dwell point of the system and 0.317 inches lateral to the centerline of the tibial bearing insert.

The model of the differently configured device was then modified with the axis of rotation 160 of the tibial bearing insert 104 to 0.317 inches lateral of the centerline 156 and 0.317 inches posterior to the dwell axis 154 (the "0.317L/0.317P configuration"). LMKS Modeling Results for the 0.317L/0.317P configuration are shown in FIG. 27 wherein the graph 350 includes lines 352 and 354 which show the estimated low (tangency) points for the lateral condylar surface 110 and the medial condylar surface 108, respectively, of the femoral component 106 on the tibial bearing insert 104. The graph 350 further includes lines 356 and 358 which show the estimated low (tangency) points for the lateral condylar surface 110 and the medial condylar surface 108, respectively, of the femoral component 106 with respect to the tibial tray 102. The lower portion of the lines 352, 354, 356, and 358 were generated as the components were moving into flexion.

The graph 350 generally shows the femoral component 106 is moving posteriorly or "rolling back" on the tibial bearing insert 104 until about 40 degrees of flexion and again from about 95 degrees of flexion to 130 degrees of flexion.

Figure 28:
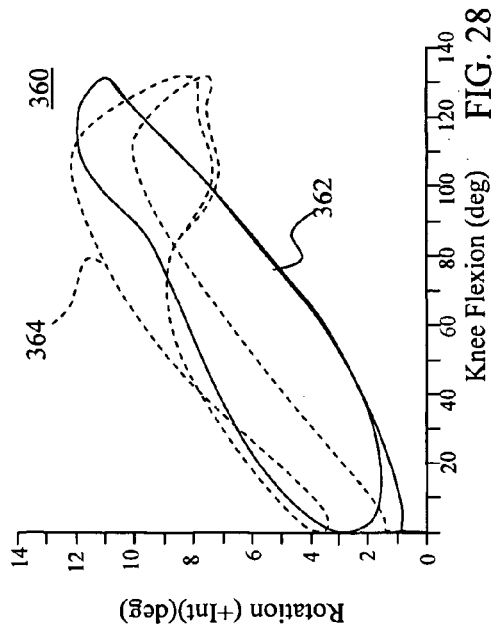
FIG. 28 shows a graph of the internal-external rotation ($\phi_{i-e}$) of the tibia with respect to the femoral component during the deep knee bending simulation of FIG. 27 along with the rotation of the tibial bearing insert with respect to the tibia.

The graph 360 of FIG. 28 includes the line 362 which identifies the $\phi_{i\text{-}e}$ of the femoral component 106 with respect to the tibia. The line 362 reveals that between 0 degrees of flexion and about 130 degrees of flexion, the $\phi_{i\text{-}e}$ for the femoral component 106 with respect to the tibia is steadily increasing to about 11 degrees. The graph 360 further includes a line 364 which identifies the rotation of the tibial bearing insert 104 with respect to the tibia. The line 364 reveals that between 0 degrees of flexion and about 110 degrees of flexion, there is a steady increase in the rotation of the tibial bearing insert 104 with respect to the tibia to about 10 degrees of rotation, followed by a slight decrease through 130 degrees of flexion.

Thus, the rotation of the tibial bearing insert 104 with respect to the tibia was greater than the $\phi_{i\text{-}e}$ for the femoral component 106 until about 120 degrees of flexion with the maximum difference in rotation between the femoral component 106 and the tibial bearing insert 104 about 3 degrees at about 60 degrees of flexion. On subsequent cycles, the rotation of the tibial bearing insert 104 with respect to the tibia was generally higher, with the maximum difference in rotation between the femoral component 106 and the tibial bearing insert 104 about 6 degrees at about 60 degrees of flexion.

The model of the differently configured device was then modified with the axis of rotation 160 of the tibial bearing insert 104 0.317 inches medial to the centerline 156 and 0.317 inches posterior to the dwell axis 154 (the "0.317M/0.317P configuration"). LMKS Modeling Results for the 0.317M/0.317P configuration are shown in FIG. 29 wherein the graph 370 includes lines 372 and 374 which show the estimated low (tangency) points for the lateral condylar surface 110 and the medial condylar surface 108, respectively, of the femoral component 106 on the tibial bearing insert 104. The graph 370 further includes lines 376 and 378 which show the estimated low (tangency) points for the lateral condylar surface 110 and the medial condylar surface 108, respectively, of the femoral component 106 with respect to the tibial tray 102.

The lower portion of the lines 372, 374, 376, and 378 were generated as the components were moving into flexion.

The graph 370 generally shows the lateral condyle element 110 of the femoral component 106 is moving posteriorly or "rolling back" on the tibial bearing insert 104 until about 60 degrees of flexion while the medial condyle 108 exhibits rollback to about 20 degrees of flexion. The femoral component 106 exhibits additional rollback from about 100 degrees of flexion to 130 degrees of flexion.

The graph 380 of FIG. 30 includes the line 382 which identifies the $\phi_{i-e}$ of the femoral component 106 with respect to the tibia. The line 382 reveals that between 0 degrees of flexion and about 130 degrees of flexion, the $\phi_{i-e}$ for the femoral component 106 with respect to the tibia is steadily increasing to almost 6 degrees. The graph 380 further includes a line 384 which identifies the rotation of the tibial bearing insert 104 with respect to the tibia. The line 384 reveals that between 0 degrees of flexion and about 50 degrees of flexion, there is a constant decrease in the rotation of the tibial bearing insert 104 with respect to the tibia to about −5 degrees, followed by a slight increase through about 130 degrees of flexion. Thus, the maximum difference in rotation between the femoral component 106 and the tibial bearing insert 104 is about 9 degrees at about 130 degrees of flexion. On subsequent cycles, the difference is less early in flexion.

The FIGS. 17-30 thus confirm that the position of the axis of rotation for a rotating plateau system may be used manage the conformity between the rotation of the plateau and the $\phi_{i-e}$ for the femoral component of the system. Additionally, the position of the axis of rotation may be used to manage the rollback and rotational characteristics of a rotating plateau system.

Figure 31:
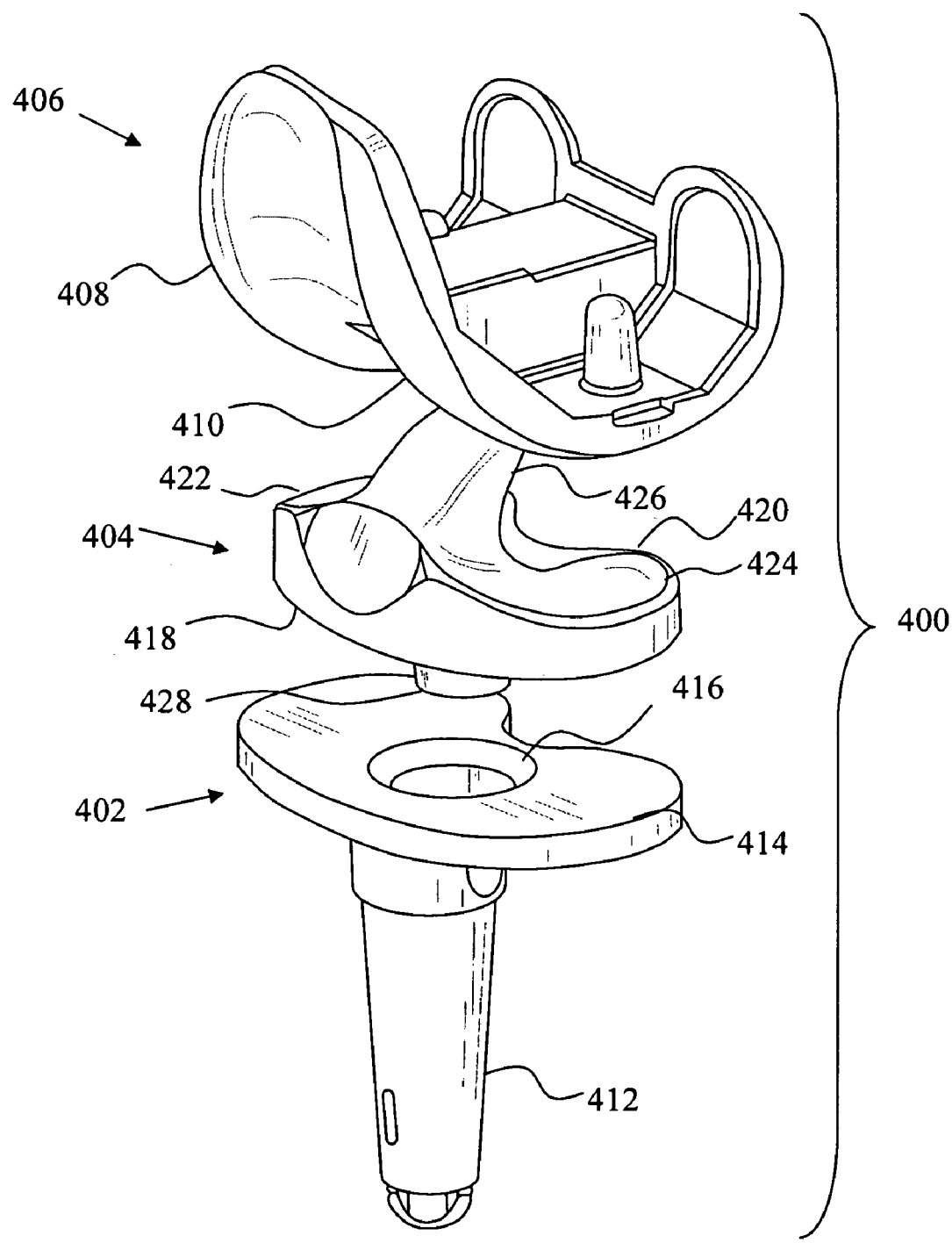
FIG. 31 depicts an exploded perspective view of a knee replacement system including a femoral component and a tibial component with a rotating plateau having an axis of rotation positioned in accordance with principles of the invention.

One embodiment of a system in accordance with principles of the invention is shown in FIG. 31. The knee replacement system 400 includes a tibial tray 402, a tibial bearing insert 404 and a femoral component 406 having two femoral condyle elements 408 and 410. The tibial tray 402 includes an inferior stem 412 for attaching the tibial tray 402 to the tibia of a patient and a superior plateau 414 for articulating with the tibial bearing insert 404. A coupling member 416 is located on the superior plateau 414.

The tibial bearing insert 404 includes an inferior tibial tray contacting surface 418 and a superior tibial bearing surface 420 The superior tibial bearing surface 420 includes a medial bearing surface 422 and a lateral bearing surface 424 configured to articulate with the femoral condyle elements 408 and 410. A spine 426 extends upwardly from between the bearing surface 422 and the bearing surface 424. A pivot 428 extends downwardly from the tibial tray contacting surface 418. The femoral component 406 may be substantially similar to the femoral component 106 and is not further described herein.

With further reference to FIG. 32, a dwell axis 430, condylar dwell points 432 and 434, and a centerline 436 of the talar bearing insert 404 are shown projected onto the superior plateau 414 and defining a dwell point 438. The coupling member 416 in this embodiment is positioned to define an axis of rotation 440 which is located posterior to the projected dwell axis 430 and lateral to the projected centerline 436. In one embodiment, axis of rotation 438 is located laterally and posteriorly from the dwell point by between about 0.2 inches and 0.5 inches. In a further embodiment, the axis of rotation 438 is located 0.317 inches posterior to the projected dwell axis 430 and 0.317 inches lateral to the projected centerline 436.

While the present invention has been illustrated by the description of exemplary processes and system components, and while the various processes and components have been described in considerable detail, applicant does not intend to restrict or in any limit the scope of the appended claims to such detail. Additional advantages and modifications will also readily appear to those ordinarily skilled in the art. The invention in its broadest aspects is therefore not limited to the specific details, implementations, or illustrative examples shown and described. By way of example, the positioning of the axis of rotation is applicable to cruciate-retaining and cruciate-sacrificing designs wherein the ACL is absent. Accordingly, departures may be made from such details without departing from the spirit or scope of the present general inventive concept. By way of example, but not of limitation, the system described herein may be applied to other joints besides the knee.

The invention claimed is:

1. A knee replacement system comprising:
   a femoral component including a lateral condylar articulating portion and a medial condylar articulating portion;
   a tibial tray including an upper articulating surface; and
   a tibial insert including (i) a first articulating portion configured to articulate with the lateral condylar articulating portion with a first condylar dwell point, (ii) a second articulating portion configured to articulate with the medial condylar articulating portion with a second condylar dwell point, (iii) a lower articulating surface configured to articulate with the upper articulating surface, and (iv) a coupling member configured to couple with the tibial tray and defining an axis of rotation about which the tibial insert rotates with respect to the tibial tray, the axis of rotation intersecting the upper articulating surface at a location posterior to a dwell axis including the first condylar dwell point and the second condylar dwell point when the dwell axis is projected onto the upper articulating surface,
   wherein the axis of rotation intersects a tibial insert centerline projected onto the upper articulating surface at a location between about 0.2 inches and about 0.5 inches posterior to the intersection of the projected centerline and the projected dwell axis.

2. The knee replacement system of claim 1, wherein the axis of rotation intersects the tibial insert centerline at a location about 0.3 inches posterior to the intersection of the projected centerline and the projected dwell axis.

3. A knee replacement system comprising:
   a femoral component including a lateral condylar articulating portion and a medial condylar articulating portion;
   a tibial tray including an upper articulating surface; and
   a tibial insert including (i) a first articulating portion configured to articulate with the lateral condylar articulating portion with a first condylar dwell point, (ii) a second articulating portion configured to articulate with the medial condylar articulating portion with a second condylar dwell point, (iii) a lower articulating surface configured to articulate with the upper articulating surface, and (iv) a coupling member configured to couple with the tibial tray and defining an axis of rotation about which the tibial insert rotates with respect to the tibial tray, the axis of rotation intersecting the upper articulating surface at a location posterior to a dwell axis including the first condylar dwell point and the second condylar dwell point when the dwell axis is projected onto the upper articulating surface, wherein the axis of rotation intersects the upper articulating surface at a location lateral to a tibial insert centerline when the centerline is projected onto the upper articulating surface, and wherein the axis of rotation intersects the upper articulating surface at a location between about 0.2 inches and about 0.5 inches away from the intersection of the projected centerline and the projected dwell axis.

4. The knee replacement system of claim 3, wherein the axis of rotation intersects the intersects the upper articulating surface at a location about 0.4 inches away from the intersection of the projected centerline and the projected dwell axis.

5. A prosthetic joint comprising:
a femoral component including a lateral condylar articulating portion and a medial condylar articulating portion;
a tibial tray including an upper articulating surface; and
a tibial insert including (i) a first articulating portion configured to articulate with the lateral condylar articulating portion, (ii) a second articulating portion configured to articulate with the medial condylar articulating portion, (iii) a lower articulating surface configured to articulate with the upper articulating surface, and (iv) a pivot defining an axis of rotation about which the tibial insert rotates with respect to the tibial tray, the axis of rotation intersecting the upper articulating surface at a location lateral to a tibial insert centerline when the centerline is projected onto the upper articulating surface, wherein the first articulating portion articulates with the lateral condylar articulating portion with a first condylar dwell point, wherein the second articulating portion articulates with the medial condylar articulating portion with a second condylar dwell point, wherein the axis of rotation intersects a dwell axis including the first condylar dwell point and the second condylar dwell point, and wherein the axis of rotation intersects a projection of the dwell axis onto the upper articulating surface at a location between about 0.2 inches and about 0.5 inches lateral to the intersection of the projected centerline and the projected dwell axis.

6. A prosthetic joint comprising:
a femoral component including a lateral condylar articulating portion and a medial condylar articulating portion;
a tibial tray including an upper articulating surface; and
a tibial insert including (i) a first articulating portion configured to articulate with the lateral condylar articulating portion, (ii) a second articulating portion configured to articulate with the medial condylar articulating portion, (iii) a lower articulating surface configured to articulate with the upper articulating surface, and (iv) a pivot defining an axis of rotation about which the tibial insert rotates with respect to the tibial tray, the axis of rotation intersecting the upper articulating surface at a location lateral to a tibial insert centerline when the centerline is projected onto the upper articulating surface, wherein the first articulating portion articulates with the lateral condylar articulating portion with a first condylar dwell point, wherein the second articulating portion articulates with the medial condylar articulating portion with a second condylar dwell point, wherein the first condylar dwell point and the second condylar dwell point define a dwell axis, wherein the axis of rotation intersects the upper articulating surface at a location posterior to a projection of the dwell axis onto the upper articulating surface, and wherein the axis of rotation intersects the upper articulating surface at a location between about 0.2 inches and about 0.5 inches away from the intersection of the projected centerline and the projected dwell axis.

7. The prosthetic joint of claim 6, wherein the axis of rotation intersects the intersects the upper articulating surface at a location about 0.4 inches away from the intersection of the projected centerline and the projected dwell axis.

8. A prosthetic joint comprising:
a femoral component including a lateral condylar articulating portion and a medial condylar articulating portion;
a tibial tray including an upper articulating surface; and
a tibial insert including (i) a first articulating portion configured to articulate with the lateral condylar articulating portion with a first condylar dwell point, (ii) a second articulating portion configured to articulate with the medial condylar articulating portion with a second condylar dwell point, (iii) a lower articulating surface configured to articulate with the upper articulating surface, and (iv) a coupling member configured to couple with the tibial tray and defining an axis of rotation about which the tibial insert rotates with respect to the tibial tray, the axis of rotation intersecting the upper articulating surface at a location posterior to a dwell axis including the first condylar dwell point and the second condylar dwell point when the dwell axis is projected onto the upper articulating surface and lateral to a tibial insert centerline when the centerline is projected onto the upper articulating surface.

9. The prosthetic joint of claim 8, wherein the axis of rotation intersects the upper articulating surface at a location between about 0.2 inches and about 0.5 inches away from the intersection of the projected centerline and the projected dwell axis.

10. The prosthetic joint of claim 9, wherein the axis of rotation intersects the intersects the upper articulating surface at a location about 0.4 inches away from the intersection of the projected centerline and the projected dwell axis.

11. The prosthetic joint of claim 10, wherein the axis of rotation intersects the upper articulating surface at a location about 0.3 inches posterior to the projected dwell axis.

12. The prosthetic joint of claim 9, wherein the axis of rotation intersects the upper articulating surface at a location about 0.3 inches posterior to the projected dwell axis.

13. The prosthetic joint of claim 9, wherein the axis of rotation intersects the upper articulating surface at a location about 0.3 inches lateral to the projected centerline.

* * * * *